(12) United States Patent
Schraermeyer

(10) Patent No.: US 9,314,453 B2
(45) Date of Patent: Apr. 19, 2016

(54) TETRAHYDROPYRIDOETHERS FOR TREATMENT OF AMD

(71) Applicant: KATAIRO GmbH, Kusterdingen (DE)

(72) Inventor: Ulrich Schraermeyer, Hechingen (DE)

(73) Assignee: Katairo GmbH, Kusterdingen (DE)

( * ) Notice: Subject to any disclaimer, the term of this patent is extended or adjusted under 35 U.S.C. 154(b) by 295 days.

(21) Appl. No.: 13/741,129

(22) Filed: Jan. 14, 2013

(65) Prior Publication Data

US 2013/0131101 A1    May 23, 2013

Related U.S. Application Data

(63) Continuation of application No. 12/863,061, filed as application No. PCT/EP2009/000248 on Jan. 16, 2009, now abandoned.

(30) Foreign Application Priority Data

Jan. 16, 2008 (EP) ..................................... 08000761
Jun. 12, 2008 (EP) ..................................... 08010697

(51) Int. Cl.
   *A61K 31/4375* (2006.01)
   *A61K 31/437* (2006.01)
   *A61K 31/50* (2006.01)

(52) U.S. Cl.
   CPC ........... *A61K 31/4375* (2013.01); *A61K 31/437* (2013.01); *A61K 31/50* (2013.01)

(58) Field of Classification Search
   CPC .......................... A61K 31/437; A61K 31/4375
   See application file for complete search history.

(56) References Cited

FOREIGN PATENT DOCUMENTS

| EP | 0 299 470 | 7/1988 |
|---|---|---|
| WO | WO 00/17200 | 3/2000 |
| WO | WO 2004/071391 | 8/2004 |
| WO | WO 2005/055926 | 6/2005 |
| WO | WO 2007/062531 | 6/2007 |
| WO | WO 2007/142626 A1 * | 12/2007 |

OTHER PUBLICATIONS

Simon et al. JPET, vol. 321, pp. 866-874, 2007.*
Bird et al.: An International Classification and Grading System for Age-Related . . . , in: Survey of Ophthalmology, vol. 39, No. 5, Mar.-Apr. 1995.
Rozanowska et al.: Photoreactivity of Aged Human RPE Melanosomes: . . . in: Investigative Ophthalmology and Visual Science, vol. 43, No. 7/2002.
Terman et al.: "Lipofuscin: Mechanisms of formation and increase with age", in: APMIS 106, 1998, pp. 265-276.
Kennedy et al.: "Lipoduscin of the retinal pigment epithelium: a review", in: Eye, vol. 9. 1995, pp. 763-771.
Holz et al.: "Progression of Geographic Atrophy and Impact . . . ", in: Amer. J. of Ophthalmology, Mar. 2007.
Schmitz-Valckenberg et al.: "Correlation between the Area of Increased . . . ", in: Investigative Ophthalmology and Visual Science, vol. 47, No. 6, Jun. 2006.
Kaminski et al.: "Antiulcer Agents. 1. Gastric Antisecretory and . . . ", in: J. Med. Chem., vol. 28, 1985, pp. 876-892.
Schmidt-Erfurth et al.: "Management of neovascular age-related macular degeneration", in: Progress in Retinal and Eye Research, No. 26, 2007, pp. 437-451.

* cited by examiner

*Primary Examiner* — Kara R McMillian
(74) *Attorney, Agent, or Firm* — Henry M. Feiereisen LLC; Ursula B. Day

(57) ABSTRACT

A medication comprising tetrahydropyridoethers for use in the treatment of AMD.

17 Claims, 22 Drawing Sheets

Fig.16

| | C | Na | P | S | Ca | Fe |
|---|---|---|---|---|---|---|
| Melanosomes in RPE from untreated monkey | 83,93±2,81<br>n=20 | 0,14±0,03<br>n=20 | 0,34±0,08<br>n=20 | 1,47±0,44<br>n=20 | 0,51±0,15<br>n=20 | 0,12±0,03<br>n=20 |
| Melanosomes in RPE from Soraprazan treated monkey 24 mg/Kg/day | 81,68±3,17<br>n=8<br>p=0,06 | 0,36±0,21<br>n=8<br>p=0,0004 | 0,50±0,05<br>n=8<br>p<0,0001 | 1,18±0,26<br>n=8<br>p=0,09 | 0,96±0,26<br>n=8<br>p<0,0001 | 0,10±0,02<br>n=8<br>p=0,25 |
| Melanosomes in macrophages from Soraprazan treated monkey 24 mg/Kg/day | 82,61±1,96<br>n=14<br>p=0,11 | 0,43±0,25<br>n=14<br>p<0,0001 | 0,53±0,07<br>n=14<br>p<0,0001 | 1,61±0,22<br>n=14<br>p=0,26 | 0,67±0,14<br>n=14<br>p=0,004 | 0,11±0,01<br>n=14<br>p=0,57 |

Fig. 17

| Group | Animal No. | Membrane stacks in RPE N = absent ++ = present, moderate number, +++ = present, high number | Microvilli in RPE N = normal, ++ = reduced number | Basal infoldings in RPE N = normal, ++ = reduced | Lysosomes in RPE N = normal | Melanosomes in RPE N = normal, ++ = fused, +++ = depigmented Lipofuscin removal ++ /+++ | Tight junctions of RPR N = normal | Rod outer segments N = normal |
|---|---|---|---|---|---|---|---|---|
| 1 (0 mg/kg/day) | 21427 M | N | N | N | N | N | N | N |
|  | 21152 F | N | N | N | N | N | N | N |
|  | 21172 F | N | N | N | N | N | N | N |
| 4 (24 mg/kg/day) | 21225 M | ++ | ++ | ++ | N | ++ | N | N |
|  | 21413 M | N | N | N | N | +++ | N | N |
|  | 21424 M | N | ++ | N | N | ++ | N | N |
|  | 21428 M | N | N | N | N | ++ | N | N |
|  | 21137 F | N | ++ | N | N | ++ | N | N |
|  | 21173 F | N | ++ | N | N | ++ | N | N |
|  | 21210 F | N | N | N | N | +++ | N | N |
| 5 (0 mg/kg/day, recovery) | 21416 M | N | N | N | N | N | N | N |
|  | 21438 M | N | N | N | N | N | N | N |
|  | 21126 F | N | N | N | N | N | N | N |
|  | 21401 F | N | N | N | N | N | N | N |
| 6 (24 mg/kg/day, recovery) | 20939 M | N | N | N | N | ++ | N | N |
|  | 21431 M | N | N | N | N | ++ | N | N |
|  | 20514 F | N | N | N | N | ++ | N | N |
|  | 21367 F | N | N | N | N | ++ | N | N |

Fig:19

TETRAHYDROPYRIDOETHERS FOR TREATMENT OF AMD

CROSS-REFERENCES TO RELATED APPLICATIONS

This application is a continuation of prior filed copending U.S. application Ser. No. 12/863,061, filed Jul. 15, 2010, the content of which is the National Phase of International application No. PCT/EP2009/000248, filed Jan. 16, 2009, which designated the United States and on which priority is claimed under 35 U.S.C. §120, and which claims the priority of European Patent Application No. 08000761.0, filed Jan. 16, 2008 and of European Patent Application No. 08010697.4, filed Jun. 12, 2008, pursuant to 35 U.S.C. 119(a)-(d).

The contents of U.S. application Ser. No. 12/863,061, PCT International application no. PCT/EP2009/000248 and European Patent Applications Nos. 08010697.4 and 08000761.0 are incorporated herein by reference in their entireties as if fully set forth therein.

BACKGROUND OF THE INVENTION

The invention relates to tetrahydropyridoethers for the treatment of AMD and claims the priority of the European Patent Application 08 000 761.0 of Jan. 16, 2008.

Age-related macular degeneration (AMD) is the main cause of blindness in the western world (Bird A C, Bressler N M, Bressler S B, Chisholm I H, Coscas G, Davis M D, de J P, Klaver C C, Klein B E, Klein R (1995) International classification and grading system for age-related maculopathy and age-related macular degeneration: Surv. Ophthalmol 39: 367-374). About 30 million people suffer from age-related macula degeneration (AMD), which leads to a loss of central vision.

The macula is the most important part of the retina. The retinal pigment endothelium (RPE) is essential for retinal function. In healthy eyes, undisturbed transport of metabolites takes place between photoreceptors and the RPE-choroid. Accumulation of material between Bruch's membrane and the RPE inhibits the transport of metabolites. Years of daily phagocytosis of the shed photoreceptor tips by RPE are thought eventually to take their toll in some individuals.

Over time, lipofuscin accumulates in the aging RPE until, in some cases, the cells are virtually engorged with this material and function is almost certainly compromised. It is generally accepted that this aging process is a causative factor in age-related macular degeneration.

Melanin

Optical measurements of the pigments of the RPE and choroid have been made in human autopsy eyes varying in age between 2 weeks and 90 years old. The choroidal melanin content increased from the periphery to the posterior pole. The RPE melanin concentration decreased from the periphery to the posterior pole with an increase in the macula. The amount of RPE Lipofuscin increased from the periphery to the posterior pole with a consistent dip at the fovea. In humans there is an inverse relationship between RPE lipofuscin concentration and RPE melanin concentration.

A biochemical examination has been carried out on the lipofuscin content, lysosomal enzyme activities and melanin level in the retina and choroid of normal human eyes. The melanin level was two to three times higher in the macular RPE and choroid than in other areas. Blue-light-induced photoreactivity of melanosomes increases with age, perhaps providing a source of reactive oxygen species and leading to depletion of vital cellular reductants, which, together with lipofuscin, may contribute to cellular dysfunction (Rozanowska M, Korytowsky W, Rozanowsky B, Skumatz C, Boulton M G, Burke J M, Sarna T Photoreactivity of aged human RPE melanosomes: a comparison with lipofuscin. Invest Ophthalmol Vis Sci 2002, 43, 2088-96).

Lipofuscin

Lipofuscin is a pigment that is formed in tissues with high oxidative stress (heart, liver, brain. eye) (Terman A, Brunk U T (1998) Lipofuscin: Mechanisms of formation and increase with age. APMIS 106: 265-276) Lipofuscin, also called age pigment, is a brown-yellow, electron-dense, autofluorescent material that accumulates progressively over time in lysosomes of postmitotic cells, such as neurons and cardiac myocytes and the RPE. The exact mechanisms behind this accumulation are still unclear. It can be detected histologically by its autofluorescence properties. The origin of lipofuscin in the RPE is still under debate (Kennedy C J, Rakoczy P E, Constable I J (1995) Lipofuscin of the retinal pigment epithelium: a review. Eye 9: 763-771). Numerous studies indicate that the formation of lipofuscin is due to the oxidative alteration of macromolecules by oxygen-derived free radicals generated in reactions catalyzed by redox-active iron of low molecular weight. Two principal explanations for the increase of lipofuscin with age have been suggested. The first one is based on the notion that lipofuscin is not totally eliminated (either by degradation or exocytosis) even at a young age, and, thus, accumulates in postmitotic cells as a function of time. Since oxidative reactions are obligatory for life, they would act as age-independent enhancers of lipofuscin accumulation, as well as of many other manifestations of senescence. The second explanation is that the increase of lipofuscin is an effect of aging, caused by an age-related enhancement of autophagocytosis, a decline in intralysosomal degradation, and/or a decrease in exocytosis. No reports state that lipofuscin can be degraded or exocytosed by RPE cells. In the eye, lipofuscin accumulates with age, especially in the RPE, and occupies a considerable part of the cell volume in elderly persons. Lipofuscin content, expressed as fluorescence intensity, in the macular retinal pigment epithelium (RPE) and choroid was two to three times higher than in other areas, and increased with aging.

Interestingly, there is an association of melanin and lipofuscin in the RPE. By use of enzyme cytochemistry, fluorescence microscopy, and lipid extraction, two types of melanin-containing complex granules have been identified: melanin with a cortex of lipofuscin (melanolipofuscin and melanin with a cortex of non-lipid, enzyme reactive material (melanolysosomes).

Lipofuscin and aged melanin in the RPE can generate oxygen radicals, and both are believed to be involved in making the RPE dysfunctional. The more lipofuscin the RPE at the margins of the geographic atrophy contains, the quicker the atrophy will progress (Holz et al. (2007) Am J Ophthalmol 143; 4639; Schmitz-Valckenberg et al 2006; IOVS 47:2648).

AMD

This correlation is well accepted in ophthalmology. If the progressing atrophy (AMD) reaches the macula, the patients become legally blind. Two forms exist: Wet AMD is characterized by neovascularization whereas dry AMD leads to geographic atrophy of the RPE and retina. Macular degeneration in both forms is associated with an accumulation of lipofuscin and melano-lipofuscin (Feeney L (1978) Lipofuscin and melanin of human retinal pigment epithelium. Fluorescence, enzyme cytochemical and ultrastructural studies. Invest. Ophthalmol. Vis. Sci. 17: 583-600), an increase in large deposits between the RPE cell layer and the Bruch's membrane (called drusen).

A high cost anti-VEGF therapy (Ranibizumab) has been developed against wet AMD.

80 to 85% of the AMD patients have dry AMD, for which no treatment modality currently exists.

It is consequently an object of the invention to provide a compound for the treatment of AMD, especially for dry AMD.

SUMMARY OF THE INVENTION

It has now been found that tetrahydropyridoethers especially, Soraprazan (INN Name) (7R,8R,9R)-2,3-Dimethyl-8-hydroxy-7-(2-methoxyethoxy)-9-phenyl-7,8,9,10-tetrahydro-imidazo[1,2-h][1,7]naphthyridine and its salts and related compounds remove lipofuscin from RPE cells and can therefore serve as active ingredient in the treatment of AMD degeneration, especially of dry AMD.

Until this observation, it was believed that the RPE cells could not eliminate their lipofuscin during life.

The compounds, including Soraprazan, used for treatment according to the invention have been described in WO 00/17200 (tetrahydropyridoethers) and EP 1 115 725 B1 that are herewith incorporated by reference. EP 1 115 725 B1 especially describes preferred compounds and methods of preparation including starting compounds described e.g. in EP-A-0 299 470 or Kaminski et. al., J. Med. Chem. 1985, 28, 876-892. The compounds according to the invention can be prepared, for example starting from N-protected 8-amino-imidazo[1,2-a]pyridines in an enantioselective synthesis as described in EP 1 115 725. The full process with different variations and examples is incorporated by reference including the examples of the final products 1-8 and starting compounds A1-D.

The invention furthermore relates to medications which contain one or more compounds described in EP 1 115 725 and/or their pharmacologically tolerable salts.

These compounds and examples for their preparations are described as follows:

The invention relates to compounds of the formula I

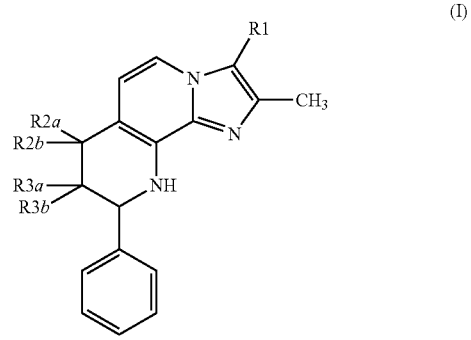

(I)

in which R1 is methyl or hydroxymethyl, one of the substituents R2a and R2b is hydrogen and the other is hydroxy, methoxy, ethoxy, isopropoxy, methoxyethoxy or methoxypropoxy, one of the substituents R3a and R3b is hydrogen and the other is hydroxy, methoxy, ethoxy, isopropoxy, methoxyethoxy or methoxypropoxy, where R2a or R2b on the one hand and R3a or R3b on the other hand are not simultaneously hydroxy, and their salts.

Suitable salts of compounds of the formula I are especially all acid addition salts. Particular mention may be made of the pharmacologically tolerable salts of the inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl) benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

Pharmacologically intolerable salts which can be initially obtained as process products, for example in the preparation of the compounds according to the invention on an industrial scale, are converted into pharmacologically tolerable salts by processes known to the person skilled in the art.

According to expert's knowledge the compounds of the invention as well as their salts may contain, e. g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

The compounds of the formula I have three chiral centers. The invention relates to all eight conceivable stereoisomers in any desired mixing ratio with one another, including the pure enantiomers, which are a preferred subject of the invention.

In a preferred embodiment of the invention compounds are used of the formula I*

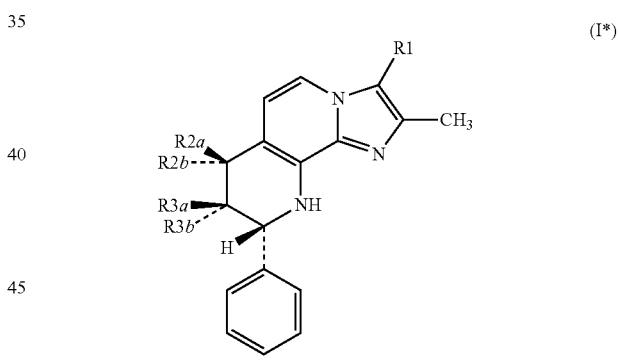

(I*)

in which R1 is methyl or hydroxymethyl, one of the substituents R2a and R2b is hydrogen and the other is hydroxy, methoxy, ethoxy, isopropoxy, methoxyethoxy or methoxypropoxy, one of the substituents R3a and R3b is hydrogen and the other is hydroxy, methoxy, ethoxy, isopropoxy, methoxyethoxy or methoxypropoxy, where R2a or R2b on the one hand and R3a or R3b on the other hand are not simultaneously hydroxy, and their salts.

An embodiment (embodiment a) of the invention are compounds of the formula I*, in which R1 is methyl, one of the substituents R2a and R2b is hydrogen and the other is methoxy, ethoxy, isopropoxy, methoxyethoxy or methoxypropoxy, one of the substituents R3a and R3b is hydrogen and the other is hydroxy, and their salts.

A further embodiment (embodiment b) of the invention are compounds of the formula I*, in which R1 is methyl, one of the substituents R2a and R2b is hydrogen and the other is hydroxy, one of the substituents R3a and R3b is hydrogen and the other is methoxy, ethoxy, isopropoxy, methoxyethoxy or methoxypropoxy, and their salts.

A further embodiment (embodiment c) of the invention are compounds of the formula I*, in which R1 is methyl, one of the substituents R2a and R2b is hydrogen and the other is methoxy, ethoxy, isopropoxy, methoxyethoxy or methoxypropoxy, one of the substituents R3a and R3b is hydrogen and the other is methoxy, ethoxy, isopropoxy, methoxyethoxy or methoxypropoxy, and their salts.

A further embodiment (embodiment d) of the invention are compounds of the formula I*, in which R1 is hydroxymethyl, one of the substituents R2a and R2b is hydrogen and the other is methoxy, ethoxy, isopropoxy, methoxyethoxy or methoxypropoxy, one of the substituents R3a and R3b is hydrogen and the other is hydroxy, and their salts.

A further embodiment (embodiment e) of the invention are compounds of the formula I*, in which R1 is hydroxymethyl, one of the substituents R2a and R2b is hydrogen and the other is hydroxy, one of the substituents R3a and R3b is hydrogen and the other is methoxy, ethoxy, isopropoxy, methoxyethoxy or methoxypropoxy, and their salts.

A further embodiment (embodiment f) of the invention are compounds of the formula I*, in which R1 is hydroxymethyl, one of the substituents R2a and R2b is hydrogen and the other is methoxy, ethoxy, isopropoxy, methoxyethoxy or methoxypropoxy, one of the substituents R3a and R3b is hydrogen and the other is methoxy, ethoxy, isopropoxy, methoxyethoxy or methoxypropoxy, and their salts.

Preferred compounds of the embodiments a to f are those, in which R3b is hydrogen.

Particularly preferred compounds of the embodiments a to f are those, in which R2a and R3b are hydrogen.

Preferred compounds within the scope of the invention are those of embodiment a, which can be characterized by the formula I**

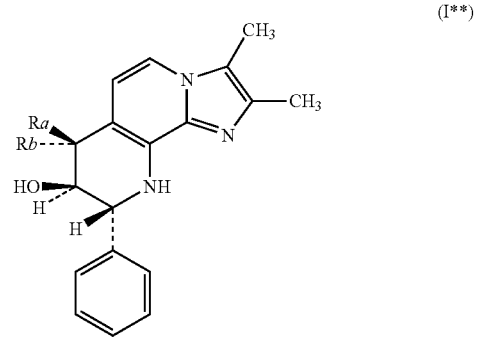

(I**)

in which one of the substituents Ra and Rb is hydrogen and the other is methoxy, ethoxy, isopropoxy, methoxyethoxy or methoxypropoxy, and their salts.

Particularly preferred compounds of embodiment a are those of formula I**, in which Ra is hydrogen and Rb is methoxy, ethoxy, isopropoxy, methoxyethoxy or methoxypropoxy, and their salts.

With the aid of the general formula I*, the following exemplary preferred compounds according to the invention may actually be mentioned by means of the substituent meanings for R1, R2a, R2b, R3a and R3b in the following Table 1 (Tab. 1):

TABLE 1

| R1 | R2a | R2b | R3a | R3b |
|---|---|---|---|---|
| $CH_3$ | H | $OCH_3$ | OH | H |
| $CH_3$ | H | $OC_2H_5$ | OH | H |
| $CH_3$ | H | $OCH(CH_3)_2$ | OH | H |
| $CH_3$ | H | $OCH_2CH_2OCH_3$ | OH | H |
| $CH_3$ | H | $OCH_2CH_2CH_2OCH_3$ | OH | H |
| $CH_3$ | H | OH | $OCH_3$ | H |
| $CH_3$ | H | OH | $OC_2H_5$ | H |
| $CH_3$ | H | OH | $OCH(CH_3)_2$ | H |
| $CH_3$ | H | OH | $OCH_2CH_2OCH_3$ | H |
| $CH_3$ | H | OH | $OCH_2CH_2CH_2OCH_3$ | H |
| $CH_3$ | H | $OCH_3$ | $OCH_3$ | H |
| $CH_3$ | H | $OC_2H_5$ | $OC_2H_5$ | H |
| $CH_3$ | H | $OCH(CH_3)_2$ | $OCH(CH_3)_2$ | H |
| $CH_3$ | H | $OCH_2CH_2OCH_3$ | $OCH_2CH_2OCH_3$ | H |
| $CH_3$ | H | $OCH_2CH_2CH_2OCH_3$ | $OCH_2CH_2CH_2OCH_3$ | H |
| $CH_2OH$ | H | $OCH_3$ | OH | H |
| $CH_2OH$ | H | $OC_2H_5$ | OH | H |
| $CH_2OH$ | H | $OCH(CH_3)_2$ | OH | H |
| $CH_2OH$ | H | $OCH_2CH_2OCH_3$ | OH | H |
| $CH_2OH$ | H | $OCH_2CH_2CH_2OCH_3$ | OH | H |
| $CH_2OH$ | H | OH | $OCH_3$ | H |
| $CH_2OH$ | H | OH | $OC_2H_5$ | H |
| $CH_2OH$ | H | OH | $OCH(CH_3)_2$ | H |
| $CH_2OH$ | H | OH | $OCH_2CH_2OCH_3$ | H |
| $CH_2OH$ | H | OH | $OCH_2CH_2CH_2OCH_3$ | H |
| $CH_2OH$ | H | $OCH_3$ | $OCH_3$ | H |
| $CH_2OH$ | H | $OC_2H_5$ | $OC_2H_5$ | H |
| $CH_2OH$ | H | $OCH(CH_3)_2$ | $OCH(CH_3)_2$ | H |
| $CH_2OH$ | H | $OCH_2CH_2OCH_3$ | $OCH_2CH_2OCH_3$ | H |
| $CH_2OH$ | H | $OCH_2CH_2CH_2OCH_3$ | $OCH_2CH_2CH_2OCH_3$ | H |
| $CH_3$ | $OCH_3$ | H | OH | H |
| $CH_3$ | $OC_2H_5$ | H | OH | H |
| $CH_3$ | $OCH(CH_3)_2$ | H | OH | H |
| $CH_3$ | $OCH_2CH_2OCH_3$ | H | OH | H |
| $CH_3$ | $OCH_2CH_2CH_2OCH_3$ | H | OH | H |
| $CH_3$ | OH | H | $OCH_3$ | H |
| $CH_3$ | OH | H | $OC_2H_5$ | H |
| $CH_3$ | OH | H | $OCH(CH_3)_2$ | H |
| $CH_3$ | OH | H | $OCH_2CH_2OCH_3$ | H |
| $CH_3$ | OH | H | $OCH_2CH_2CH_2OCH_3$ | H |

TABLE 1-continued

| R1 | R2a | R2b | R3a | R3b |
|---|---|---|---|---|
| $CH_3$ | $OCH_3$ | H | $OCH_3$ | H |
| $CH_3$ | $OC_2H_5$ | H | $OC_2H_5$ | H |
| $CH_3$ | $OCH(CH_3)_2$ | H | $OCH(CH_3)_2$ | H |
| $CH_3$ | $OCH_2CH_2OCH_3$ | H | $OCH_2CH_2OCH_3$ | H |
| $CH_3$ | $OCH_2CH_2CH_2OCH_3$ | H | $OCH_2CH_2CH_2OCH_3$ | H |
| $CH_2OH$ | $OCH_3$ | H | OH | H |
| $CH_2OH$ | $OC_2H_5$ | H | OH | H |
| $CH_2OH$ | $OCH(CH_3)_2$ | H | OH | H |
| $CH_2OH$ | $OCH_2CH_2OCH_3$ | H | OH | H |
| $CH_2OH$ | $OCH_2CH_2CH_2OCH_3$ | H | OH | H |
| $CH_2OH$ | OH | H | $OCH_3$ | H |
| $CH_2OH$ | OH | H | $OC_2H_5$ | H |
| $CH_2OH$ | OH | H | $OCH(CH_3)_2$ | H |
| $CH_2OH$ | OH | H | $OCH_2CH_2OCH_3$ | H |
| $CH_2OH$ | OH | H | $OCH_2CH_2CH_2OCH_3$ | H |
| $CH_2OH$ | $OCH_3$ | H | $OCH_3$ | H |
| $CH_2OH$ | $OC_2H_5$ | H | $OC_2H_5$ | H |
| $CH_2OH$ | $OCH(CH_3)_2$ | H | $OCH(CH_3)_2$ | H |
| $CH_2OH$ | $OCH_2CH_2OCH_3$ | H | $OCH_2CH_2OCH_3$ | H |
| $CH_2OH$ | $OCH_2CH_2CH_2OCH_3$ | H | $OCH_2CH_2CH_2OCH_3$ | H |

And the salts of these compounds.

The compounds according to the invention can be prepared as described by way of example in the following examples, or using analogous process steps starting from appropriate starting compounds (see, for example, EP-A-0 299 470 or Kaminski et al., J. Med. Chem. 1985, 28, 876-892). The starting compounds are known or can be prepared analogously to the known compounds. The compounds according to the invention can be prepared for example starting from N-protected 8-amino-imidazo[1,2-a]pyridines according to the following reaction scheme:

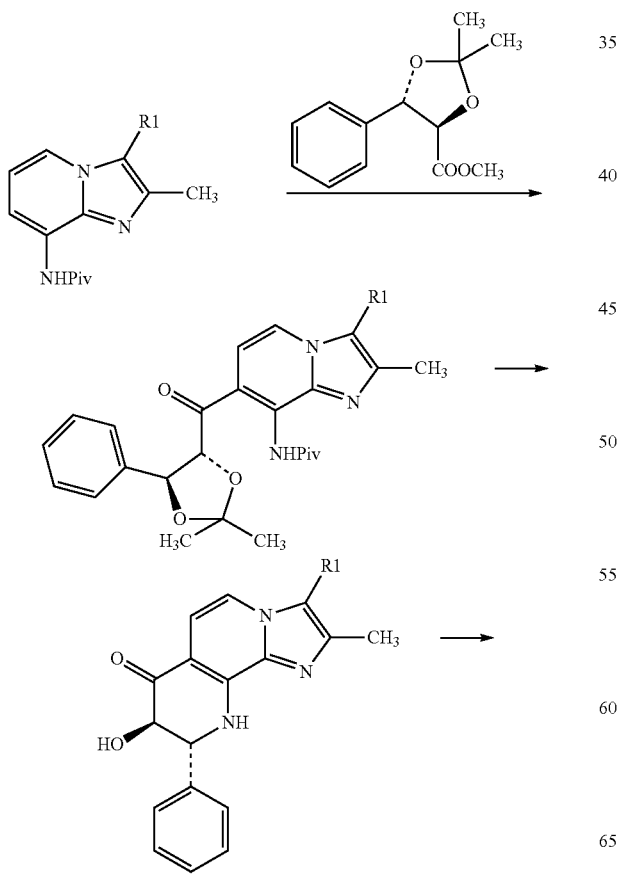

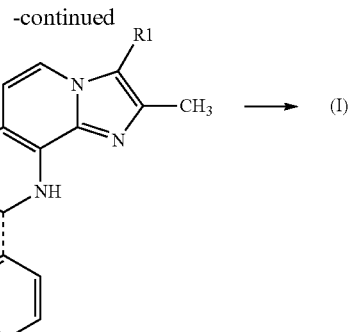

The above scheme represents an example of an enantioselective synthesis. The N-protected (Ply represents a customary protective group, preferably the pivaloyl group), 8-aminoimidazo[1,2-a]pyridine deprotonated in the 7-position is reacted with an enantiomerically pure dioxolane. This initially leads to a condensation product which can be cyclized under strongly acidic conditions with removal of the protecting groups. The subsequent reduction of the keto group using sodium borohydride leads in over 90% enantiomeric purity to the 7,8-trans-diol indicated. The subsequent etherification which is carried out according to known processes, e. g. as described in the Examples, leads to the final products of formula I* in which R2a and R3b are hydrogen. The corresponding 7,8-cis-compound is obtained from the mother liquor, which is left after separating off the 7,8-trans-compound, by chromatographic purification.

The substances according to the invention are isolated and purified in a manner known per se, for example, by distilling off the solvent in vacuo and recrystallizing the residue obtained from a suitable solvent or subjecting it to one of the customary purification methods, such as, for example, column chromatography on suitable support material.

Salts are obtained by dissolving the free compound in a suitable solvent, e. g. in a chlorinated hydrocarbon, such as dichloromethane or chloroform, or a low molecular weight aliphatic alcohol (ethanol, isopropanol) which contains the desired acid, or to which the desired acid is subsequently added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically intolerable salts can be converted into pharmacologically tolerable salts.

The pure enantiomers, in particular the pure enantiomers of the formula I*, to which the invention preferably relates, can be obtained in a manner familiar to the person skilled in the art, for example by enantioselective synthesis (see, for example, the Scheme), by chromatographic separation on chiral separating columns, by derivatization with chiral auxiliary reagents, subsequent separation of diastereomers and removal of the chiral auxiliary group, by salt formation with chiral acids, subsequent separation of the salts and liberation of the desired compound from the salt, or by (fractional) crystallization from a suitable solvent. Trans-products obtained (with R2a and R3b=hydrogen) can be converted (at least partly) to the corresponding cis-products (with R2b and R3b=hydrogen) by standing under acidic conditions (e. g. 2 equivalents of acid, such as sulfuric acid) in the corresponding alcohol R2a-OH. Likewise, cis-products obtained can be converted to the corresponding trans-products. The cis- and trans-products are separated e. g. by chromatography or by crystallization.

DETAILED DESCRIPTION OF PREFERRED EMBODIMENTS

The following examples serve to illustrate the invention further without restricting it. Likewise, further compounds of the formula I whose preparation is not described explicitly can be prepared analogously or in a manner familiar to the person skilled in the art using customary process techniques. The abbreviation min stands for minute(s), h for hour(s) and ee for enantiomeric excess.

EXAMPLES

Final Products 1A. (7R,8R,9R)-2,3-Dimethyl-8-hydroxy-7-methoxy-9-phenyl-7,8,9,10-tetrahydro-imidazo[1,2-h][1,7]naphthyridine Method a 20 g (65 mmol) of (7R,8R,9R)-2,3-dimethyl-7,8-dihydroxy-9-phenyl-7,8,9,10-tetrahydro-imidazo[1,2-h][1,7]naphthyridine are dissolved in methanol (350 ml). 13.5 g of sulfuric acid are added and the solution is stirred for 48 h at 50 C. After cooling the reaction mixture is poured into 250 ml of water. The pH is adjusted by aqueous saturated sodium hydrogen carbonate solution to neutral pH. The precipitate is collected and purified on silica gel (eluent: diethylether). 2.5 g of the title compound are obtained as colourless crystals of melting point 164-165° C. (2-propanol).

Method b 10 g (32.5 mmol) of (7R,8R,9R)-2,3-dimethyl-7,8-dihydroxy-9-phenyl-7,8,9,10-tetrahydro-imidazo[1,2-h][1,7]naphthyridine are dissolved in 200 ml of dry dimethylformamide. 1.9 g of commercially available sodium hydride in paraffin (80%) are added in small portions at room temperature. After 1 h 9.1 g (65 mmol) of methyl iodide, dissolved in 4 ml of dimethylformamide, are added and the mixture is stirred for an additional hour. The reaction mixture is poured into cold water. 20 ml of a saturated aqueous ammonium chloride solution is added; the yellow precipitate is collected and discarded. The filtrate is extracted several times with ethyl acetate, the combined organic phases are washed several times with water and the solvent is evaporated in vacuo. The solid residue is purified on silica gel (diethylether).

2 g of the title compound are obtained as colourless crystals of melting point 164-165° C. (2-propanol).

1B. (7S,8S,9S)-2,3-Dimethyl-8-hydroxy-7-methoxy-9-phenyl-7,8,9,10-tetrahydro-imidazo[1,2-h][1,7]naphthyridine The title compound of melting point 161-162° C. is obtained similarly to the procedure described in Example 1, Method a, using (7S,8S,9S)-2,3-Dimethyl-7,8-dihydroxy-9-phenyl-7,8,9,10-tetrahydroimidazo[1,2h][1,7]naphthyridine as starting material.

2A. (7S,8R,9R)-2,3-Dimethyl-8-hydroxy-7-methoxy-9-phenyl-7,8,9,10-tetrahydro-imidazo[1,2-h][1,7]naphthyridine 6 g of the title compound are obtained as colourless powder of melting point 108-110° C. after purification on silica gel according to Example 1A, Method a, starting from (7S,8R,9R)-2,3-Dimethyl-7,8-dihydroxy-9-phenyl-7,8,9,10-tetrahydro-imidazo[1,2-h][1,7]naphthyridine.

2B. (7R,8S,9S)-2,3-Dimethyl-8-hydroxy-7-methoxy-9-phenyl-7,8,9,10-tetrahydro-imidazo[1,2-h][1,7]naphthyridine The title compound of melting point 171-172° C. is obtained from the mother liquor of Example 1B after purification on silica gel (eluent: diethyl ether).

3. (7R,8R,9R)-2,3-Dimethyl-7-ethoxy-8-hydroxy-9-phenyl-7,8,9,10-tetrahydro-imidazo[1,2-h][1,7]naphthyridine 500 mg of the title compound are obtained by reaction of (7R,8R,9R)-2,3-dimethyl-7,8-dihydroxy-9-phenyl-7,8,9,10-tetrahydro-imidazo[1,2-h][1,7]naphthyridine with ethanol and sulfuric acid according to Example 1, Method a, after purification on silica gel (eluent: diethylether). Melting point: 188-190° C.

4. (7S,8R,9R)-2,3-Dimethyl-7-ethoxy-8-hydroxy-9-phenyl-7,8,9,10-tetrahydro-imidazo[1,2-h][1,7]naphthyridine 800 mg of the title compound of melting point 135-137° C. are obtained as a solid by further purification of the mother liquor of Example 3 on silica gel.

5A. (7R,8R,9R)-2,3-Dimethyl-8-hydroxy-7-(2-methoxyethoxy)-9-phenyl-7,8,9,10-tetrahydro-imidazo[1,2-h][1,7]naphthyridine Method a 5 g of the title compound of melting point 130-131° C. are obtained by reaction of 20 g (7R,8R,9R)-2,3-dimethyl-7,8-dihydroxy-9-phenyl-7,8,9,10-tetrahydro-imidazo[1,2-h][1,7]naphthyridine with 2-methoxy-ethanol according to Example 1, Method a.

Method b

To a solution of 100 g of (7R,8R,9R)-2,3-Dimethyl-7,8-dihydroxy-9-phenyl-7,8,9,10-tetrahydroimidazo[1,2h][1,7]naphthyridine in 1 L of 2-ethoxyethanol, 64 g of concentrated. sulfuric acid are added slowly at room temperature under an argon atmosphere. The rate of addition is such that the temperature of the mixture does not exceed 35° C. After further 15 hours of stirring at room temperature the greenish solution is poured into a mixture of 1 kg of crushed ice and 800 ml of dichloromethane. The pH of the stirred mixture is adjusted to 7.5 by addition of a 10 M aqueous sodium hydroxide solution, the organic layer is separated off, the aqueous layer is extracted three times with dichloromethane (200 ml each), the dichloromethane layers are washed collectively with 500 ml of water (six times) and are then dried over sodium sulfate. After complete evaporation of the solvent under reduced pressure the remaining oily residue is treated with 450 ml of acetone to yield 75 g off-white crystals consisting of a 1:1 mixture of the title compound and its (7S,8R, 9R)-epimer. The mixture is separated by preparative HPLC using methanol as eluent. 28 g of the title compound of melting point 128-129° C. are obtained after recrystallization from ethyl acetate.

5B. (7S,8S,9S)-2,3-Dimethyl-8-hydroxy-7-(2-methoxyethoxy)-9-phenyl-7,8,9,10-tetrahydro-imidazo[1,2-h][1,7]naphthyridine The title compound of melting point 130-131° C. is obtained similarly to the procedure described in Example 5A, Method a, using (7S,8S,9S)-2,3-Dimethyl-7,8-dihydroxy-9-phenyl-7,8,9,10-tetrahydroimidazo[1,2][1,7]naphthyridine as starting material.

6A. (7S,8R,9R)-2,3-Dimethyl-8-hydroxy-7-(2-methoxyethoxy)-9-phenyl-7,8,9,10-tetrahydro-imidazo-imidazo[1,2][1,7]naphthyridine 7.8 g of the title compound of melting point 131-132° C. are obtained as a solid from the mother liquor of Example 5A after purification on silica gel (eluent: diethyl ether).

6B. (7R,8S,9S)-2,3-Dimethyl-8-hydroxy-7-(2-methoxyethoxy)-9-phenyl-7,8,9,10-tetrahydro-imidazo[1,2-h][1,7]naphthyridine The title compound of melting point 131-132° C. is obtained from the mother liquor of Example 5B after purification on silica gel (eluent: diethyl ether).

7. (7S,8R,9R)-2,3-Dimethyl-8-hydroxy-9-phenyl-7-(2-propoxy)-7,8,9,10-tetrahydro-imidazo[1,2-h][1,7]naphthyridine 1 g of the title compound of melting point 168-9 C is obtained by reaction of 3 g of (7R,8R,9R)-2,3-di-methyl-7,8-dihydroxy-9-phenyl-7,8,9,10-tetrahydro-imidazo[1,2-h][1,7]naphthyridi-ne with 2-propanol according to Example 1, Method a.

8. (7R,8R,9R)-2,3-Dimethyl-7,8-dimethoxy-9-phenyl-7,8,9,10-tetrahydro-imidazo[1,2-h][1,7]naphthyridine 8 g of the title compound of melting point 155-156° C. are obtained by reaction of 10 g of (7R,8R,9R)-2,3-dimethyl-7,8-dihydroxy-9-phenyl-7,8,9,10-tetrahydro-imidazo[1,2-h][1,7]naphthyridine with 1.9 g of sodium hydride (80%) and 9.1 g of methyl iodide according to Example 1, Method b.

Starting Compounds

A1. 2,3-Dimethyl-7-[(2R,3S)-2,3-O-isopropylidene-3-phenylpropan-1-on-1-yl]-8-pivaloylamino-imidazo[1,2-a]pyridine 60 g (0.245 mol) of 2,3-dimethyl-8-pivaloylaminoimidazo[1,2-a]pyridine are dissolved in 1.5 L of anhydrous diethyl ether with exclusion of moisture and under an argon atmosphere and cooled to −75° C. By means of a flex needle, 408 ml (0.612 mol) of tert-butyllithium solution (1.5 M in n-pentane) are added dropwise such that the temperature does not exceed −65° C. (30 min). A red suspension is formed. After addition is complete, the suspension is stirred at −75° C. for further 30 min. ⅓ of a solution of 145 g of methyl(2R,3S)-2,3-O-isopropylidene-3-phenylpropionate (ee: 99.05%, Daicel Chiralcel HPLC) in 150 ml of dry THF is then slowly added dropwise at a temperature below −65° C. during the course of 30 min. The residual quantity is then briskly added (5 min), a temperature rise to −60° C. taking place. After addition is complete the cooling bath is removed. On reaching an internal temperature of −30° C., 20 ml of methanol are added and at an internal temperature of 0° C. 200 ml of distilled water are added. The aqueous phase is separated off in a separating funnel, the organic phase is washed five times with 100 ml of distilled water each time, then the organic phase is extracted three times with 10% strength sulfuric acid (200 ml, 50 ml, 50 ml). The sulfuric acid phases are combined, treated with 200 ml of dichloromethane and adjusted to pH 2.3 with 10N sodium hydroxide solution and with ice cooling and vigorous stirring. The organic layer is separated off. The aqueous phase is extracted with 30 ml of dichloromethane. The combined dichloromethane phases are washed twice with a little distilled water. The organic layer is then dried over anhydrous sodium sulfate and the solvent is completely stripped off in vacuo. A brown oil is obtained which is treated with 50 ml of diethyl ether. After seeding, crystals are formed which are filtered off after standing overnight and washed with diethyl ether. After drying in vacuo, 57.7 g (52.5%, ee>99%, Daicel Chiralcel HPLC) of the title compound of melting point 76-80° C. are obtained as a pale yellow powder.

A2. 2,3-Dimethyl-7-[(2S,3R)-2,3-O-isopropylidene-3-phenylpropan-1-on-1-yl]-8-pivaloylamino-imidazo[1,2-a]pyridine The title compound (ee: 98.3%, Daicel Chiralcel HPLC) is obtained similarly to the procedure described in example A1 by using methyl(2S,3R)-2,3-O-isopropylidene-3-phenylpropionate (ee: 98%, Daicel Chiralcel HPLC) as acylating agent.

B1. (8R,9R)-2,3-Dimethyl-8-hydroxy-9-phenyl-7,8,9,10-tetrahydroimidazo[1,2-h][1,7]naphthyridin-7-one 10.8 g (24 mmol) of 2,3-dimethyl-7-[(2R,3S)-2,3-O-isopropylidene-3-phenyipropan-1-on-1-yl]-8-pivaloylaminoimidazo[1,2-a]pyridine (ee>95%, Daicel Chiralcel HPLC) are introduced into 50 ml of 70% strength sulfuric acid with ice cooling during the course of 4 min. A suspension is formed in the course of this, which turns into an orange solution after 30 min. After addition is complete, the ice bath is removed and the mixture is stirred on at room temperature. The reaction solution is added after 50 h to ice water and dichloromethane is added, then the mixture is adjusted to pH 8 using 6N sodium hydroxide solution and saturated sodium hydrogen-carbonate solution. The organic phase is separated off. The aqueous phase is extracted twice with dichloromethane. The organic phases are combined and washed with a little distilled water. The organic layer is then dried over anhydrous sodium sulfate, filtered and concentrated on a vacuum rotary evaporator. The concentrated residue is chromatographed on silica gel (eluent: dichloromethane/methanol 100/1). The main fraction is concentrated and treated with ethyl acetate, and the title compound crystallizes in the course of this as a yellow solid. This precipitate is filtered off with suction and dried to constant weight in a vacuum drying oven at 50° C. 4.22 g (57%, ee>95%, Daicel Chiralcel HPLC) of the title compound of melting point 231-234° C. are obtained.

B2. (8S,9S)-2,3-Dimethyl-8-hydroxy-9-phenyl-7,8,9, 10-tetrahydroimidazo[1,2-h][1,7]naphthyridin-7-one The title compound (ee: 94.0%, Daicel Chiralcel HPLC) is obtained according to the procedure described in example B1 starting from 2,3-dimethyl-7-[(2S,3R)-2,3-O-isopropylidene-3-phenylpropan-1-on-1-yl]-8-pivaloylaminoimidazo[1,2-a]pyridine.

C1. (7R,8R,9R)-2,3-Dimethyl-7,8-dihydroxy-9-phenyl-7,8,9,10-tetrahydroimidazo[1,2-h][1,7]-naphthyridine 6 g (19.52 mmol) of (8R,9R)-2,3-dimethyl-8-hydroxy-9-phenyl-7,8,9,10-tetra-hydroimidazo-[1,2-h][1,7]naphthyridin-7-one (ee>90%, Daicel Chiralcel HPLC) are suspended in 60 ml of methanol and cooled to −5 to 0° C. in a methanol-ice bath. At this temperature, sodium borohydride (0.81 g, 21.47 mmol) is added by spatula during the course of 0.5 h (evolution of gas). After addition is complete, the mixture is stirred for a further 10 min, and then concentrated in a vacuum rotary evaporator at a bath temperature of 40° C. The oily residue obtained is taken up in distilled water and extracted three times with chloroform. The organic phases are combined and washed with a little water, then dried using anhydrous sodium sulfate and filtered. The filtrate is concentrated on a vacuum rotary evaporator and co-evaporated with acetone; the title compound crystallizes out in the course of this. The precipitate is filtered off, washed with acetone and dried to constant weight at 50° C. in a vacuum drying oven. 5.15 g (85.3%, ee>90%, Daicel Chiralcel HPLC) of the title compound are obtained as a colorless crystallizate of melting point 206-9° C.

C2. (7S,8S,9S)-2,3-Dimethyl-7,8-dihydroxy-9-phenyl-7s8,9f 1o-tetrahydroimidazo[1,2-h][1,7]naphthyridine The title compound of mp 207-208° C. (ee: 98.7%, Daicel Chiralcel HPLC) is obtained according to the procedure described in example C1 using (8S,9S)-2,3-dimethyl-8-hydroxy-9-phenyl-7,8,9,10-tetrahydroimidazo[1,2-h][1,7]naphthyridin-7-one as starting material.

D. (7S,8R,9R)-2,3-Dimethyl-7,8-dihydroxy-9-phenyl-7,8,9,10-tetrahydro-imidizo[1,2-h][1,7]naphthyridine 2 g of the mother liquor of Example C1 are chromatographed on silica gel (eluent:ethyl acetate/methanol 19/1) to give 0.35 g of the title compound as an oil which crystallizes upon addition of ethyl acetate. Melting point: 199-200° C. (ethyl acetate).

The medication according to the invention is prepared by processes known per se, which are familiar to the person skilled in the art. As medication, the pharmacologically active compounds according to the invention are employed either as such, or preferably in combination with suitable pharmaceutical auxiliaries or excipients in the form of intraocular devices, where the active compound content is advantageously and where, by the appropriate choice of the auxiliaries and excipients, a pharmaceutical administration form exactly suited to the active compound and/or to the desired onset of action can be achieved.

The person skilled in the art is familiar, on the basis of his expert knowledge, with auxiliaries or excipients which are suitable for the desired pharmaceutical formulations.

The active compounds are preferably administered orally, topically, intravitreally, subretinally or periocularly. It has proven advantageous to administer the active compound(s) in a dose from 10-50 ng/ml. Favourably a dosage of about 10 to about 50 mg/kg body weight, in particular about 10 to about 40 mg/kg, more preferably of about 10 to about 36 mg/kg body weight is administered to the patient. The optimal dose and manner of administration of the active compounds necessary in each case can easily be determined by any person skilled in the art on the basis of his expert knowledge.

If the compounds according to the invention and/or their salts are to be employed for the treatment of the above mentioned diseases, the pharmaceutical preparations can also contain one or more pharmacologically active constituents of other pharmaceutical groups.

Soraprazan was administered in oral application of 6, 12 and 24 mg/kg/day for 52 weeks in the Cynomolgus monkey.

Some monkeys from the control and the high-dose group were subjected to a recovery period of 3 months.

Conventional histopathology revealed no alterations after treatment with 6 and 12 mg/kg/day. Three out of 12 monkeys treated with 24 mg/kg/day, including 1 animal with a funduscopic abnormality, showed migration of individual macrophages either beneath the RPE (1 animal), and/or into the subretinal space (3 animals). Two of these 3 monkeys had depigmentation of RPE cells although the photoreceptors facing the depigmented RPE stayed healthy. These RPE cells had released melanin as well as lipofuscin granules to secondary cells that had migrated between Bruch's membrane and the RPE cell layer or into the subretinal space.

Therefore this shows that it is possible to stop the progression of lipofuscin accumulation in conditions where there is a risk of getting dry AMD.

As lipofuscin can be easily detected in the fundus, the invention would also allow prevention of the disease, as detection can already be done at an early stage of the disease development.

Description of Examples

In the present example the effect of Soraprazan on pigmentation of the retinal pigment epithelium in the Cynomolgus monkey (4 years of age) after oral application of 24 mg/kg/day for 52 weeks is shown.

Methods

Right eyes from the following animals were subjected to transmission electron microscopy:

| Group | Soraprazan (mg/kg/day) 52 weeks | No. of animals investigated by transmission electron microscopy m/f |
|---|---|---|
| 1 | 0 | 3/4 |
| 2 | 24 | 4/3 |

Sampling, Fixation, Embedding

Right eyes were removed carefully. A circular slit was cut at the limbus in order to immerse the inner eye with the fixation fluid (5% Glutaraldehyd in 100 µmol Cacodylat buffer). From these eyes, specimens (1 mm$^3$ in diameter) from the macula and from the mid-area were cut out, were postfixed in OsO$_4$, treated with uranylacetate, dehydrated and embedded in Epon resin.

Sectioning, Evaluation

Semithin sections (0.7 µm) were prepared from Epon resin blocks. They were stained with toluidin blue and evaluated under a light microscope. Subsequently, ultrathin sections (50 nm) were cut from Epon resin blocks, contrasted and evaluated in a transmission electron microscope.

Ultrastructure of RPE and Photoreceptor Outer Segments in Control Animals

The RPE cells of the Cynomolgus monkeys contain many microvilli at the apical cell surface. Spindle-shaped melanin granules are located in normal RPE within these microvilli. The spindle shaped melanosomes are 1.6 µm long and 0.5-0.7 µm thick. The central parts of the RPE cells contain predominately round melanosomes and lipofuscin granules with a diameter between 0.7-1.2 µm in most cases. Also many mixed type granules (melanolipofuscin) containing both melanin and lipofuscin are present in the central parts of the RPE cells. The outer segments of cones contain irregular disk membranes and homogenous material, whereas the outer segments of the rods contain more regularly shaped and highly ordered disk membranes.

Treatment-Related Findings in RPE Cells and Photoreceptor Cells

Ultrastructural alterations in the retina compared to untreated monkeys could not be detected in any of the treated monkeys (Table 1).

TABLE 1

Summary of ultrastructural findings

| Group | Animal No. | Lipofuscin removal from RPE N = normal, ++ = moderate +++ = complete | RPE cell morphology (except pigment granules) N = normal | Structure of photo-receptors N = normal |
|---|---|---|---|---|
| 1 (0 mg/kg/day) | 1 | N | N | N |
| | 2 | N | N | N |
| | 3 | N | N | N |
| | 4 | N | N | N |
| | 5 | N | N | N |
| | 6 | N | N | N |
| | 7 | N | N | N |
| 2 (24 mg/kg/day) | 8 | +++ | N | N |
| | 9 | +++ | N | N |
| | 10 | ++ | N | N |
| | 11 | ++ | N | N |
| | 12 | ++ | N | N |
| | 13 | ++ | N | N |
| | 14 | +++ | N | N |

Lysosomes in RPE cells exhibited a regular morphology. Accumulation of secondary lysosomes which degrade the shed tips of the outer segments were not found in any RPE cells investigated in this study. RPE cells did not divide, nor did they show any signs related to cell death.

Tight junctions between RPE cells appeared normal in all groups. Separation of RPE cells or enlargement of intercellular clefts between RPE cells was not observed in any eye from this study.

Example 1

The most prominent alteration was loss of melanin and lipofuscin in RPE cells in the eyes of 3 out of 7 monkeys from animals treated with 24 mg/kg/day (Table 1). Different stages of degradation of spindle shaped melanosomes within the apical microvilli were observed.

These spindle shaped melanosomes became 0.4-0.2 µm thin and then separated into bead-like structures, before dividing up into separate individual small granules with diameters between 0.2-0.5 µm. Finally the spindle shaped granules disappear completely from the microvilli. In these animals there were many areas with a diameter up to 2 micrometers in which the RPE was more or less completely free of melanin and lipofuscin granules. Such areas were also observed below the macula. In addition, fusion of melanosomes in large lysosomes was observed in all 7 monkeys that were investigated from group 2.

Example 2

In the vicinity of depigmented RPE cells, macrophage-like cells were frequently present. Staining with CD 68 antibodies showed that these cells were macrophages. They were located in most cases between Bruch's membrane and RPE. They were also seen within Bruch's membrane. These macrophages were filled with lipofuscin granules and melanosomes as well as melanolipofuscin granules and therefore were highly pigmented. Pigment granules within these macrophages were often collected in lysosomes. These findings show that the RPE cells can release their pigment granules.

Example 3

Section was illuminated under the fluorescence microscope with 360 nm wavelength light. Lipofuscin granules were detected by the emission of gold-yellow light with 540 µm wavelength. In RPE cells that were depigmented by bright light examination, the lipofuscin granules were completely or almost completely absent. Macrophages between the RPE and Bruch's membrane, however, contained many lipofuscin granules. The majority of these granules were smaller than those in RPE cells of untreated animals. These findings show that the RPE cells can release their pigment granules.

Example 4

The number of lipofuscin granules that were smaller than 0.4 µm in diameter was counted in the cytoplasm of ultrathin sections of RPE cells from untreated and treated monkeys. In addition the same counts were performed in macrophages located between RPE and Bruch's membrane of treated monkeys. The results were 4.9±0.6/50 µm$^2$, 0.6±0.2/50 µm$^2$; 13.6±0.9150 µm$^2$. Lipofuscin granules larger than 1 µm in diameter were absent in RPE cells of treated animals. In contrast many of them were present in RPE cells of untreated monkeys. These findings show that the RPE cells of treated monkeys can eliminate the lipofuscin granules.

Example 5

In order to investigate whether trace element concentration is altered by drug administration, X-ray microanalysis of melanosomes within RPE cells from untreated and drug treated monkeys was performed. In addition melanosomes within macrophages were also analysed.

An increase of the Na, P and Ca concentration and a statistically insignificant decrease of Fe was found in RPE melanosomes after treatment with Soraprazan. These results show that pigment granules are chemically modified by Soraprazan treatment. This may be the reason why the pigment granules are extruded from the RPE cells.

No morphological changes in the neuroretina were observed at the ultrastructural level after treatment with Soraprazan 24 mg/kg/day for 52 weeks.

The present study shows for the first time that RPE cells of the adult monkey can eliminate lipofuscin and degrade melanin. Both findings were induced by drug administration. These findings are extremely unusual and surprising, because until this finding it was believed that the RPE cells could not eliminate their lipofuscin during life.

Therefore, with the present invention it is possible to prevent the progression of lipofuscin accumulation or to remove lipofuscin in patients at risk of getting AMD, especially dry AMD.

As lipofuscin can be easily detected in the fundus, this new treatment method can already be applied at an early stage of the disease development of dry and wet AMD.

Example 6

Retinal pigment epithelium (RPE) cells from human donor eyes were cultured and exposed permanently to either vehicle solution, solution of Soraprazan or solution of 7R,8R,9R)-2,3-Dimethyl-7-ethoxy-8-hydroxy-9-phenyl-7,8,9,10-tetrahydro-imidazo-[1,2-h][1,7]-naphthyridin (called substance 1) at a concentration of 50 µg/ml or 0.25 mM. At several time points, digital images were taken and analysed with respect to the portion of lipofuscin and pigmentation in general. As the results did strongly depend on the random choice of microscopic field and the variations of the data were very high, the values of four consecutive days of five independent experiments were averaged. The results for the lipofuscin content in the RPE cells are shown in the diagram (FIG. 18).

Retinal pigment epithelium (RPE) cells from human donor eyes were cultured and exposed permanently to either vehicle solution, solution of Soraprazan or solution of substance 1 (concentration 50 µg/ml or 0.25 mM). At several time points, digital images were taken and analysed with respect to the portion of lipofuscin and pigmentation in general.

The degree of lipofuscin content and total pigmentation decreases slightly in the control samples, which can be explained by a weak division of RPE cells and thus dilution of pigment. In the cell cultures treated with Soraprazan, lipofuscin and pigment content are decreased compared to the control. In the RPE cells treated with substance 1, there was an even more clear and significant decrease in both lipofuscin content and pigmentation.

Then the treatment-dependent ability of the cells to phagocytose, which is a crucial function of the RPE, was checked. For this purpose, RPE cell cultures from human donor eyes were exposed to vehicle or substance 1. After three weeks, fluorescent latex beads were added to the cell cultures for four hours. The cells were then washed to remove non-phagocytosed beads and fixed. Fluorescent images of the cells were taken and analysed for the contents of lipofuscin and the number of phagocytosed beads. The results shown in FIG. 19 are presented as the relationship between lipofuscin content and phagocytosed bead number in both controls and substance-1-treated cells.

It can clearly be seen that the RPE cells contain much more lipofuscin under control conditions than under the influence of substance 1. In addition, it is obvious that RPE cells of a high lipofuscin content do not phagocytose many latex beads, in most cases not a single one. In contrast, many cells with a small portion of lipofuscin have phagocytosed a significantly higher number of latex beads.

As a summary of the in vitro experiments, it can be concluded that the human RPE cells get rid of their lipofuscin when they are treated with Soraprazan or substance 1, and that loss of lipofuscin is associated with an enhanced ability of phagocytosis.

Example 7

The effects of lipofuscin in vivo, i.e. in the living eye of experimental rats after an intravitreal injection of the compounds were investigated. Vehicle solution or solutions of either substance 1 or Soraprazan were injected intravitreally in half-year old Wistar rats. The final concentration in the vitreous was the same as in the cell cultures, i.e. 50 µg/ml or 0.25 mM. In order to avoid mutual interactions between the two eyes of an animal, both eyes of an animal were treated the same way, with three animals (i.e. six eyes) per group.

Two kinds of evaluation were performed in these animals—electroretinography (ERG) for functional testing, and counting of lipofuscin particles to check whether the administration of the compounds leads to a decrease of lipofuscin contents in the RPE.

Electroetinography:

Before the injection, electroretinograms were measured to obtain base line values. Additional ERG measurements were performed one, two and three weeks after the intravitreal injections. Some results are shown in the diagrams below.

The ERG amplitudes obtained one week after the injection were smaller than the base line values, in most cases significantly. Such a decrease is a direct consequence of the injection procedure and has been observed also in other studies were intravitreal injection has been performed, and the extent of the decrease depended on the kind of injected solution and the kind of electroretinographic parameter.

In the diagrams (FIG. 20), changes of the amplitudes of a-waves and b-waves are shown, recorded at the highest intensity of light stimulation. After an injection of vehicle solution (containing 20 vol % DMSO), a decrease of amplitudes is observed. If Soraprazan or substance 1 are injected, the decrease of the amplitudes is even more pronounced. During the following time, a certain recovery of the amplitudes can be observed. Amplitudes obtained in animals treated with vehicle or substance 1 solutions did recover almost completely three weeks after the injection, whereas the values obtained in Soraprazan-treated animals remained significantly lower than the base line. Such a behaviour was also seen in the photopic b-waves, i.e. the cone-driven response of the post-receptoral systems.

The amplitudes of the scotopic oscillatory potentials did not show a recovery after the initial decrease in all three groups, and the same is true for the 30-Hz Flicker response. There is obviously a permanent damage by the injection that cannot be repaired, probably by the DMSO that is present in the injected solution. The kind of damage suggests that inner neurones and/or the communication between them may be disturbed.

As a summary, the used compounds interfere with the function of the photoreceptors and post-receptoral systems. Nevertheless, disturbance of retinal function was almost reversible compared to vehicle-injected eyes if substance 1 had been used. Less side effects on retinal function can be expected by reduction of DMSO content in the injected solution and an optimised injection routine.

Lipofuscin Content:

The eyes were isolated after three weeks, fixed in formalin and embedded in paraffin. Paraffin sections were made, and digital fluorescence images were evaluated. The number of fluorescent lipofuscin particles per 50 μm RPE layer length was counted. The results are shown in the diagram (FIG. 21).

In the vehicle-treated eyes, 21.0±7.8 lipofuscin particles were found per 50 μm. In contrast, only 15.0±8.3 particles were found in Soraprazan-treated eyes, and 9.8±6.1 particles in eyes treated with substance 1. The difference between these values was significant. Consequently, even one single injection of the compounds leads to a clear decrease in the lipofuscin content in the RPE.

Example 8

Heavily pigmented human donor RPE cells (passage)) were treated with 50 μg/ml substance 1 or 30 μg/ml Soraprazan and cultured for 28 days. Cells without treatment were used as controls. Cells were fixed for electron microscopy in 2% glutaraldehyde and embedded in EPON. Semithin and ultrathin sections were cut.

Ultrastructurally, treated cells contained big clusters of pigment-like granules (FIG. 22), covered by a limiting membrane. Individual lipofuscin, melanin or melanolipofuscin granules were missing, but were present in the controls. These clusters contained unusual small melanin granules embedded into a lipofuscin-like electron opaque matrix. The total amount of normal appearing pigment granules was largely reduced in these cells. In treated cells many small electron lucent and opaque granules were present. Clusters and the electron lucent granules could only infrequently be observed in the controls.

In the semithin sections, the clusters could be observed as well. Here, the pigmented cells bearing one or more clusters were counted. Degradational clusters were detected in 90.5%+/−21.3 of cells treated with substance 1 and in 80.1%+/−22.6 of cells treated with Soraprazan, but only in 16.8%+/−21.6 of untreated cells (p<0.0001).

Thus, the pigments undergo degradation in substance treated human RPE cells.

BRIEF DESCRIPTION OF THE DRAWINGS

FIG. 3, in contrast to FIG. 2 shows that RPE from young individuals contains many melanosomes. Lipofuscin granules are absent. The arrow marks a melanin granule in the RPE. The arrowhead indicates a melanin granule within a choroidal melanocyte. R=rod outer segment; N=nucleus; C=choriocapillaris; B=Bruch's membrane; I=basal labyrinth.

FIG. 10 shows a light micrograph under fluorescent light from the RPE of a monkey which was treated with Soraprazan. Only few lipofuscin granules are present (white arrow). In some cells they are completely removed (arrow head).

FIG. 16:
The concentration of C, Na, P, S, Ca and Fe in RPE melanosomes or in melanosomes from macrophages after drug treatment are presented in atom % as detected by EDX. These findings were compared to the concentrations without treatment. A significant increase of Ca, Na and P was found in RPE melanosomes after treatment. (p=p-values from Student's T-test; n=number of measurements). The animal was treated with 24 mg Soraprazan/kg/day.

FIG. 17:
The table shows that lipofuscin depigmentation in the RPE was observed in monkeys treated with 24 mg Soraprazan/kg/day. The morphology of the photoreceptors as judged by the ultrastructure of the outer segments was normal. This indicates that the function of the RPE was not altered, although some mild changes were seen in the microvilli and basal labyrinth.

Figure 1:
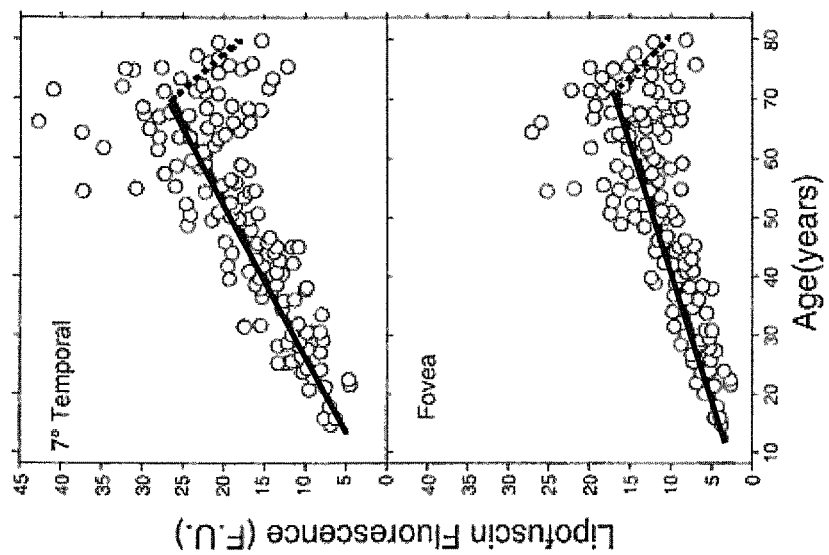
FIG. 1:
Lipofuscin fluorescence as a function of age at 7° temporal to the fovea (top) and at the fovea (bottom). The solid lines are linear regression lines for ages 20 to 70 years (P<0.0001). The interrupted lines are linear regression lines for ages 70 to 80 years (P<0.12). From Delori F C, Goger D G, Dorey C K Age-related accumulation and spatial distribution of lipofuscin in RPE of normal subjects. Invest Ophthalmol Vis Sci. 2001; 42:1855-66.
Figure 2:
FIG. 2:
RPE from a 72 year old women contains few melanosomes, but many lipofuscin (black arrow) or melanolipofuscin granules (white arrow).
Figure 3:
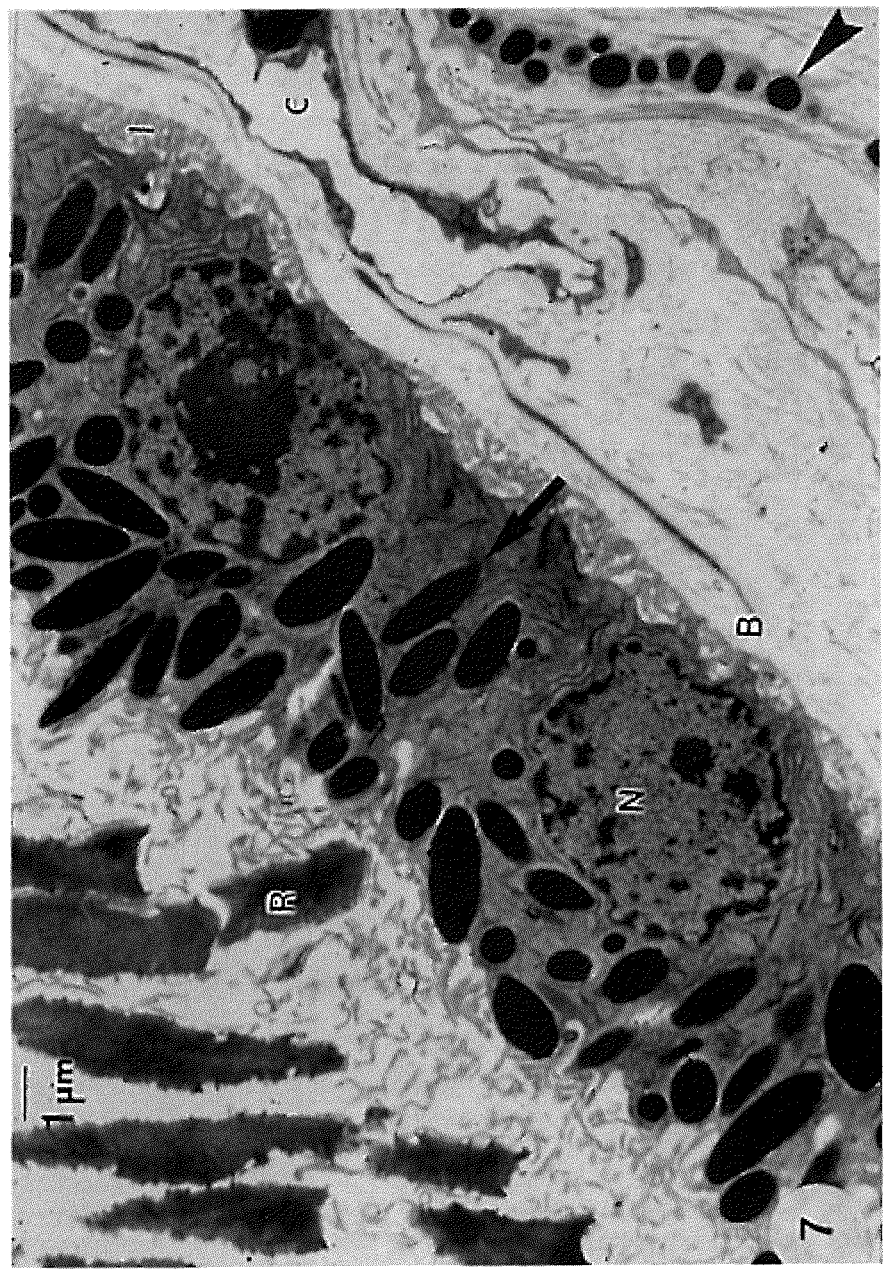
FIG. 3.
Figure 4:
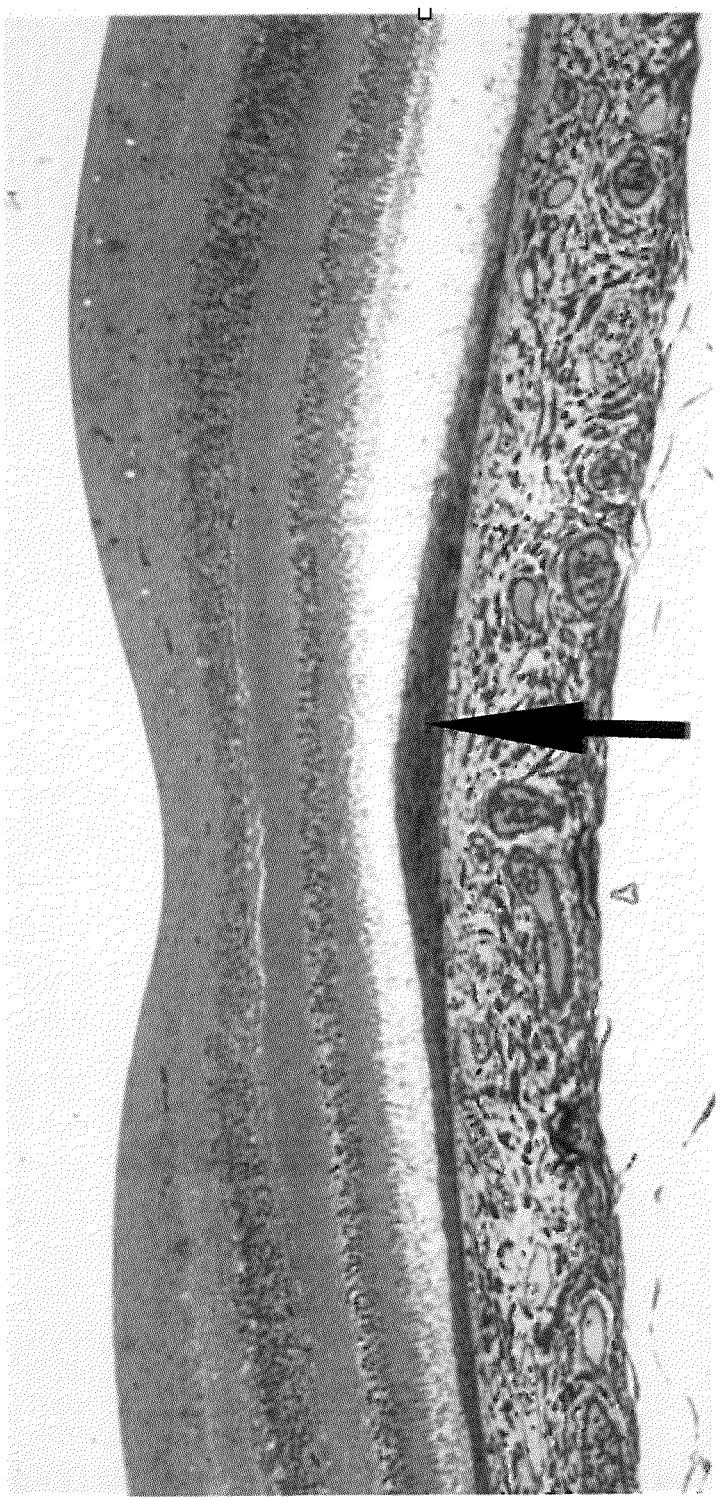
FIG. 4:
Several macrophages (arrow) have migrated between Bruch's membrane and RPE just below the macula of a monkey after treatment with Soraprazan. Whereas the RPE is nearly free of lipofuscin, the macrophages are highly pigmented (see also FIG. 5 for more details). The photoreceptors appear healthy.
Figure 5:
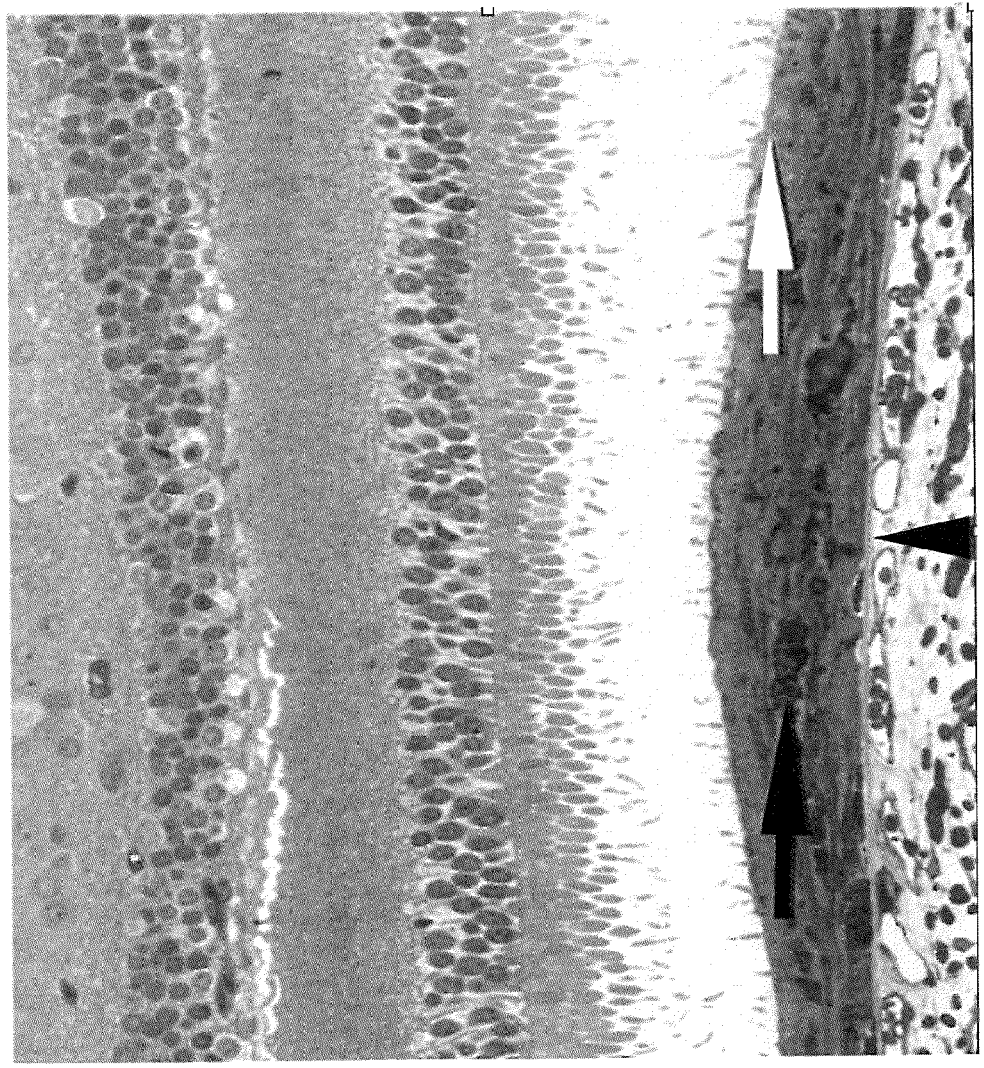
FIG. 5:
Several macrophages (black arrow) have migrated between Bruch's membrane and RPE just below the macula of a monkey after treatment with Soraprazan. Whereas the RPE is nearly free of Lipofuscin (white arrow), the macrophages are highly pigmented. The photoreceptors appear healthy.
Figure 6:
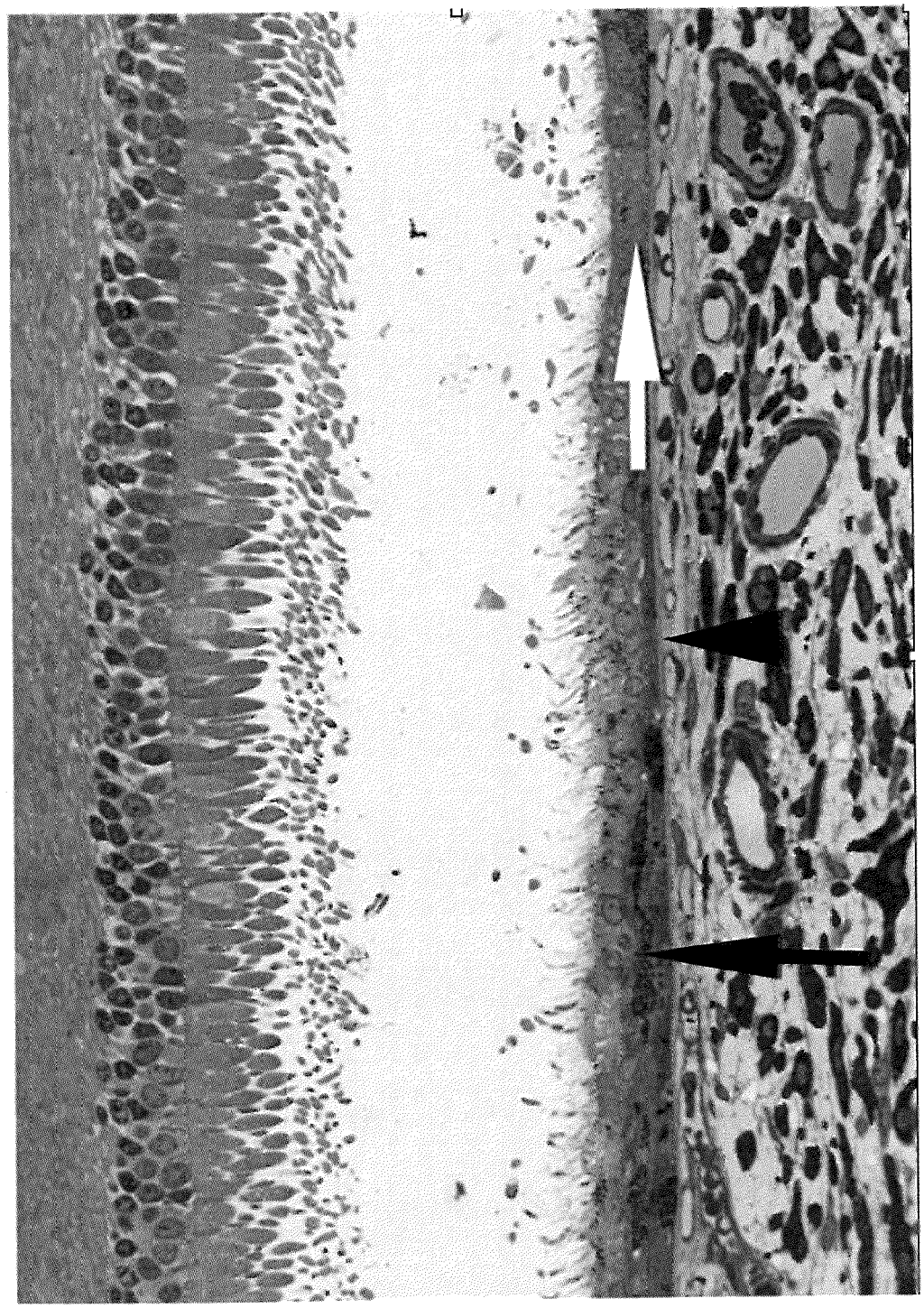
FIG. 6:
The normal pigmented RPE of an untreated monkey is shown (top). After treatment with Soraprazan the RPE is nearly free of lipofuscin (arrow), which is now localised within the macrophage (bottom; black arrow). Arrowhead: Bruch's membrane).
Figure 7:
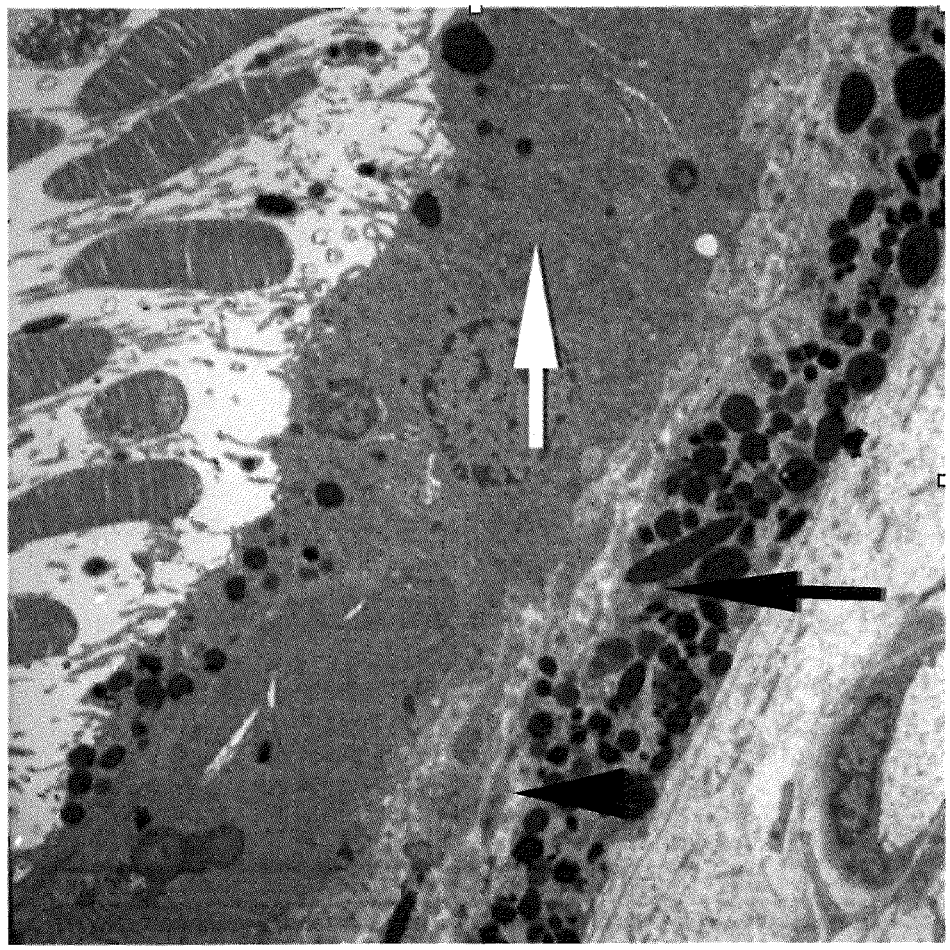
FIG. 7:
A macrophage (black arrow) is localised between Bruch's membrane and the RPE of a monkey after treatment with Soraprazan, as shown in an electron micrograph. The RPE is nearly free of lipofuscin (white arrow), which is now localised within the macrophage (FIG. 9) below. Rod outer segments appear normal.
Figure 8:
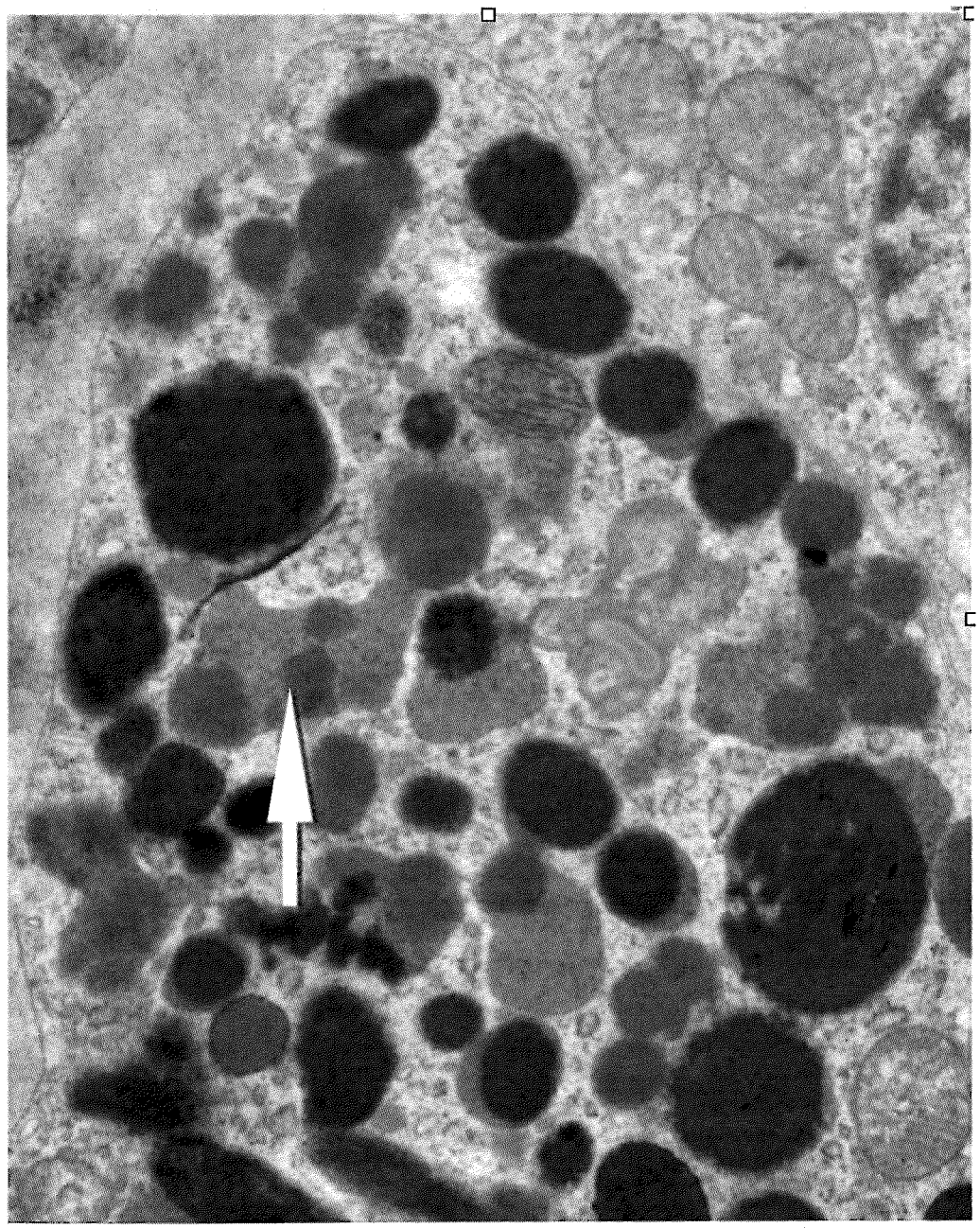
FIG. 8:
Ultrathin section from a monkey treated with Soraprazan reveals a trilayer of cells in the parafovea shown in a semithin section in FIG. 6. Blood vessels are not present in this layer. The morphology of the choriocapillaris and Bruch's membrane is normal. The cells are separated by an extracellular matrix. The outer segments of the photoreceptors are completely normal. The RPE has lost melanin and lipofuscin granules. Lipofuscin granules (arrow) are visible within a macrophage.
Figure 9:
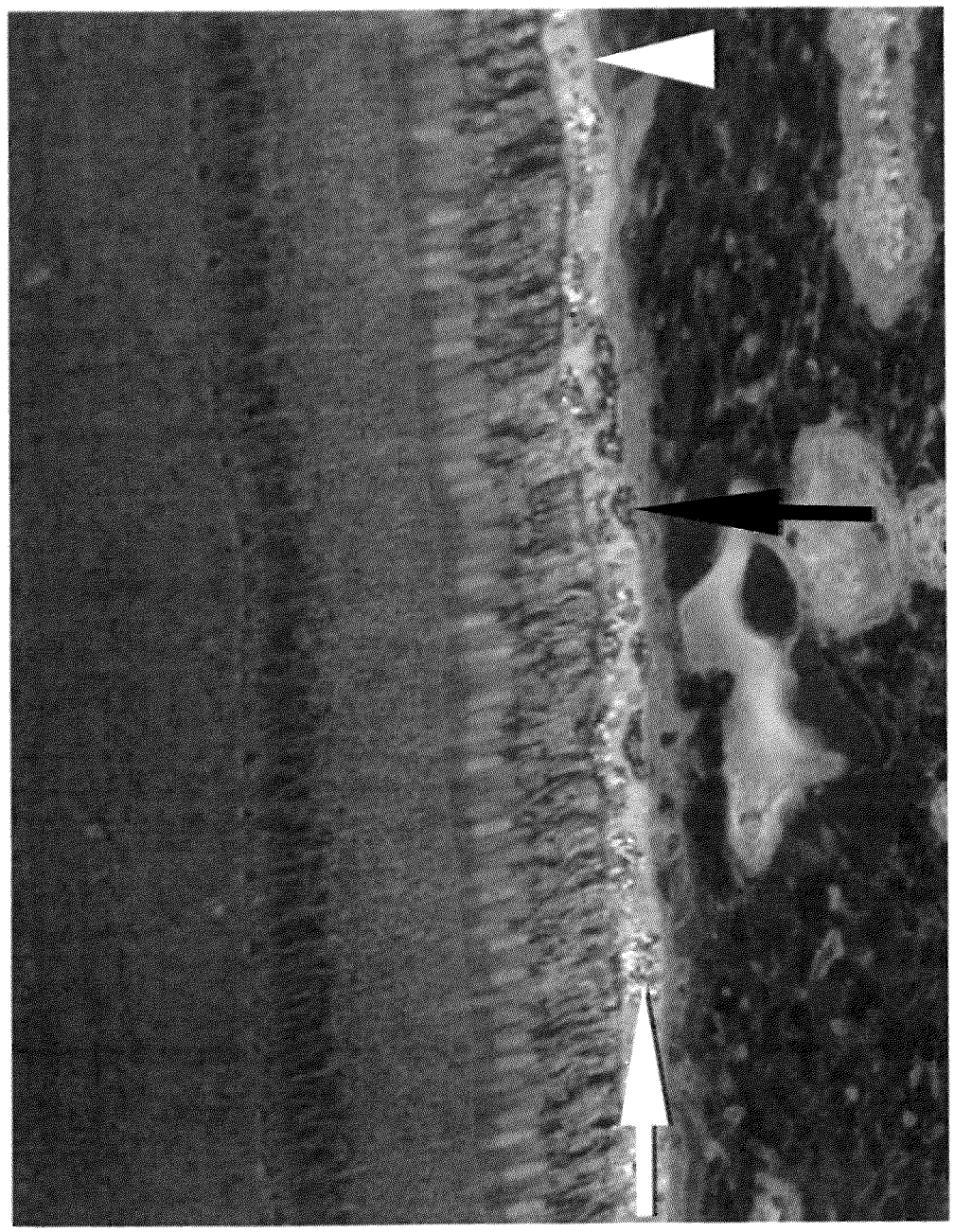
FIG. 9:
Ultrathin section from a monkey treated with Soraprazan shows small lipofuscin granules within a macrophage localised between Bruch's membrane and the RPE. Such lipofuscin granules within macrophages were measured and counted and compared to those within the RPE cells of untreated monkeys (see FIG. 15). One RPE cell (white arrow) contains the normal quantity of melanin and lipofuscin. Other RPE cells have lost lipofuscin completely (arrowhead). Macrophages that have taken up lipofuscin are located between Bruch's membrane and RPE (black arrow).
Figure 10:
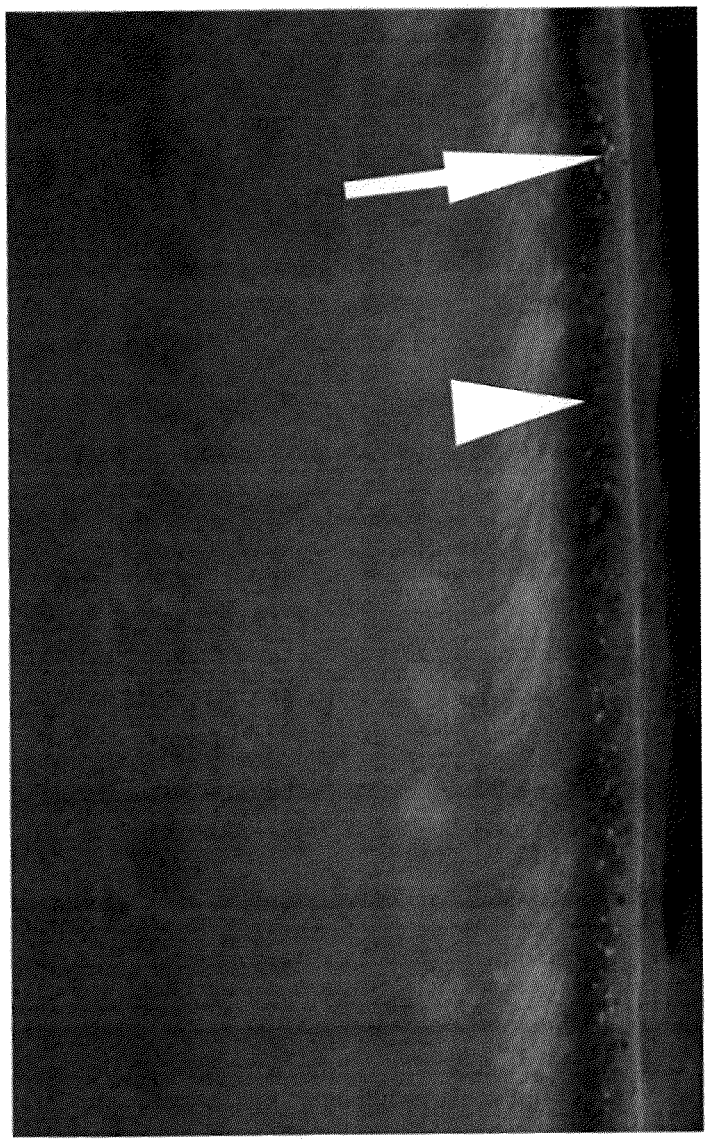
FIG. 10.
Figure 11:
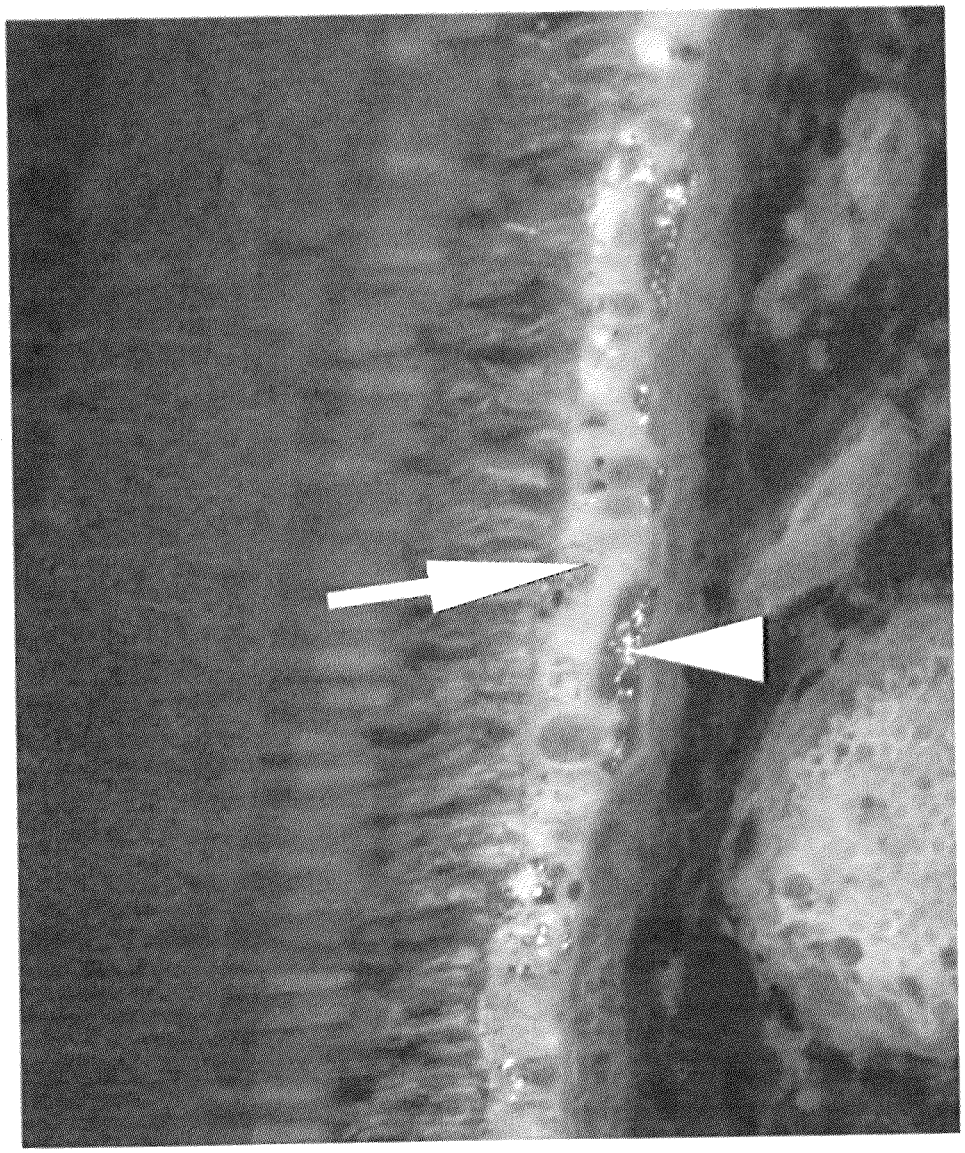
FIG. 11:
The arrow head shows macrophages located between Bruch's membrane and the RPE which had taken up lipofuscin granules from RPE cells. The lipofuscin granules are identified by their golden-yellow autofluorescence in a light micrograph. The RPE cells are nearly free of lipofuscin granules (arrow). The rod outer and inner segments of the photoreceptors appear normal.
Figure 12:
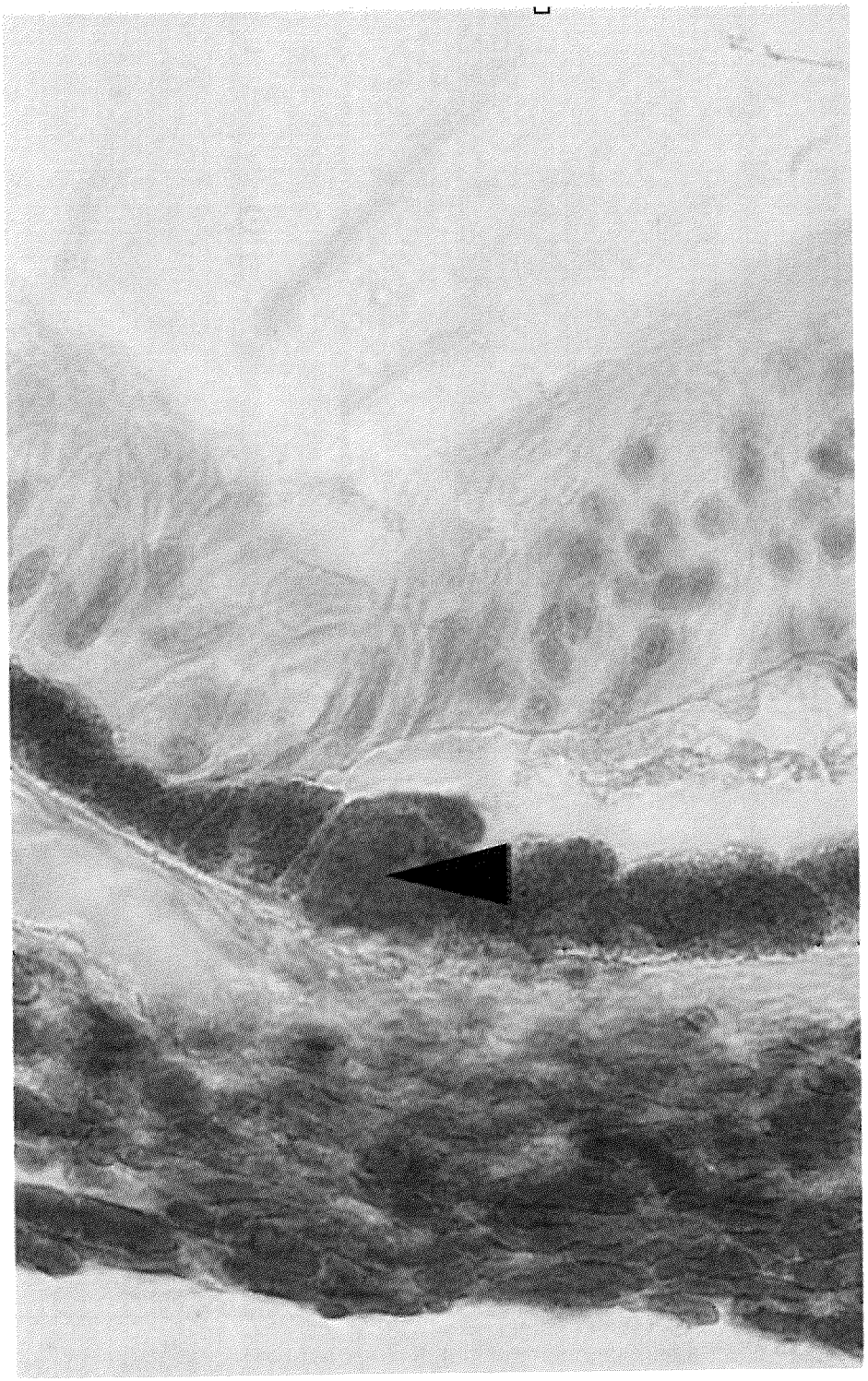
FIG. 12:
Paraffin section from a monkey treated with Soraprazan. A macrophage (arrow) identified by immunostaining with CD 68 antibodies has migrated between Bruch's membrane and RPE.
Figure 13:
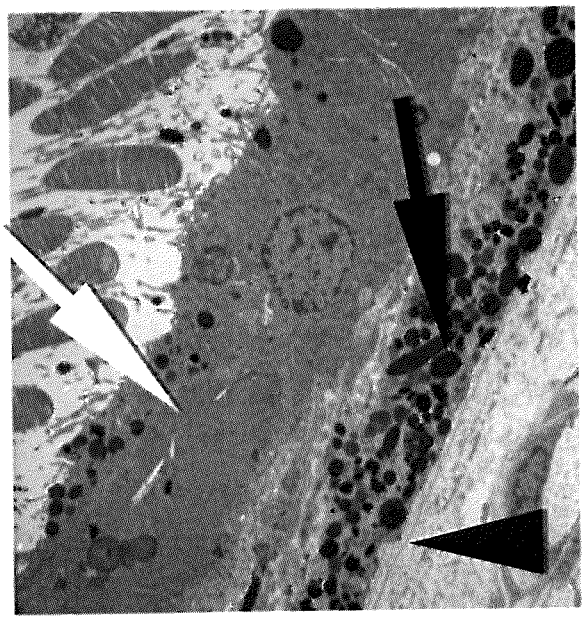
FIG. 13:
Ultrathin section from a monkey treated with Soraprazan shows small lipofuscin granules within a macrophage (black arrow) localised between Bruch's membrane (arrowhead) and the RPE. The RPE cell has lost melanin and lipofuscin from the cytoplasm (white arrow).
Figure 14:
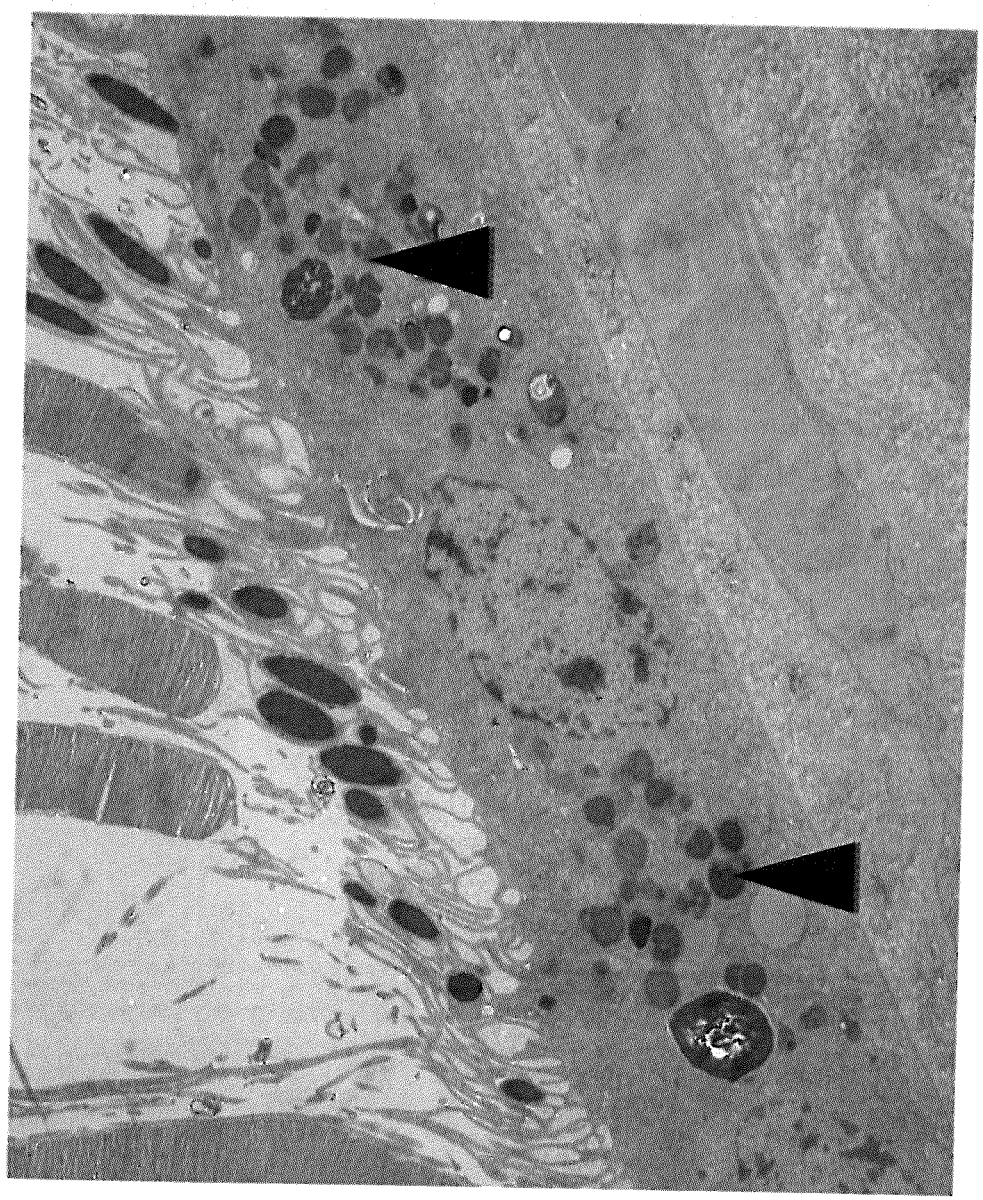
FIG. 14:
Ultrathin section of RPE cells of monkey not treated Soraprazan (Control). The RPE cells contain many lipofuscin and melanolipofuscin granules (arrowheads).
Figure 15:
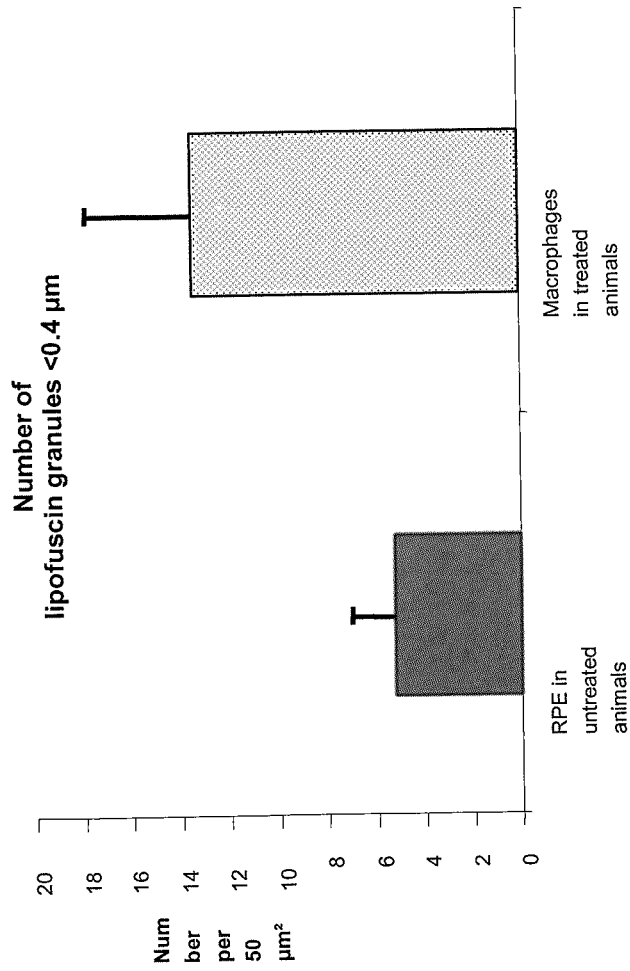
FIG. 15:
The lipofuscin granules within macrophages of FIG. 13 were measured and counted and compared to those of FIG. 14. The number of small lipofuscin granules is significantly enhanced in macrophages indicating degradation after Soraprazan treatment.
Figure 18:
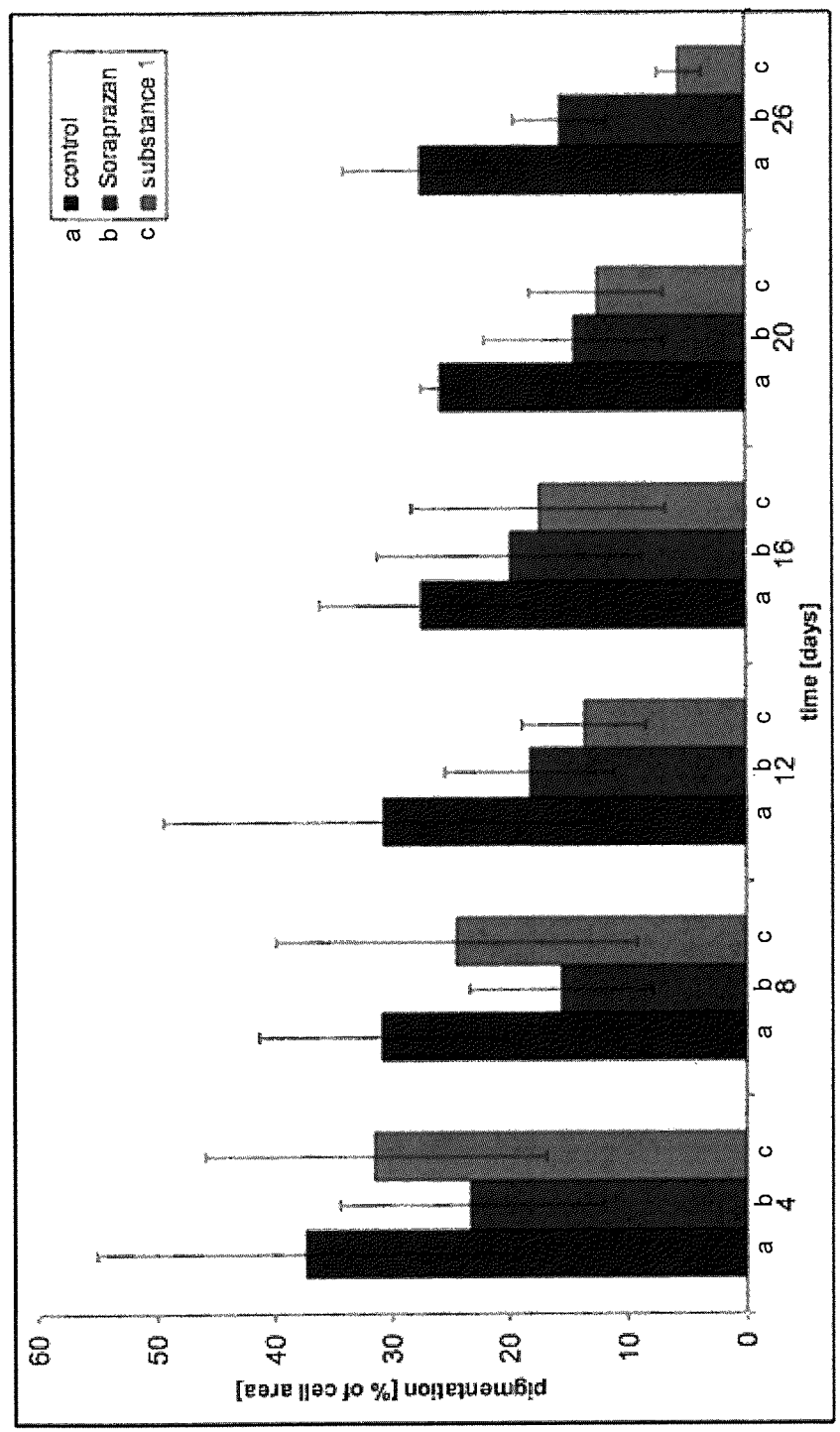
FIG. 18:
Lipofuscin and melanin is reduced in cultured human RPE cells after 26 days of treatment with Soraprazan and substance 1. (a) control, (b) Soraprazan, (c) substance 1.
Figure 19:
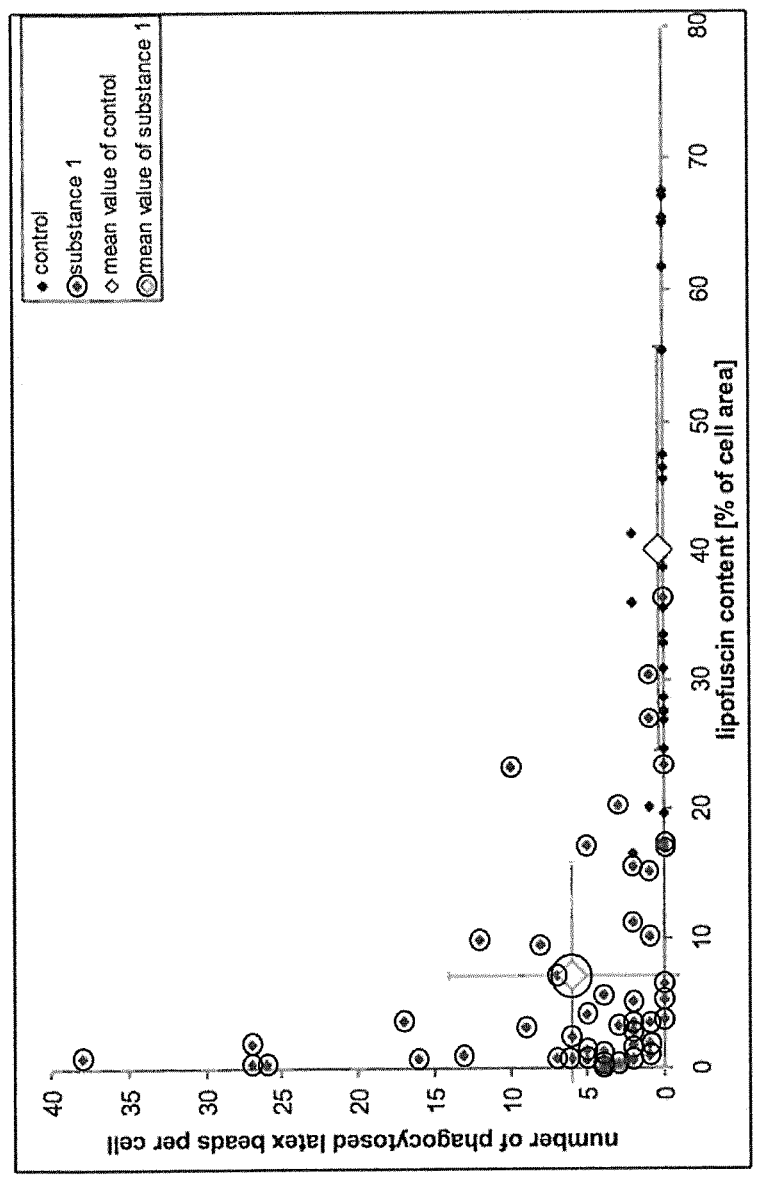
FIG. 19:
The results shown in this diagram are presented as the relationship between lipofuscin content and phagocytosed bead number in both controls and substance-1-treated human RPE cells. Treated and depigmented cells phagocytosed more beads than untreated cells.
Figure 20:
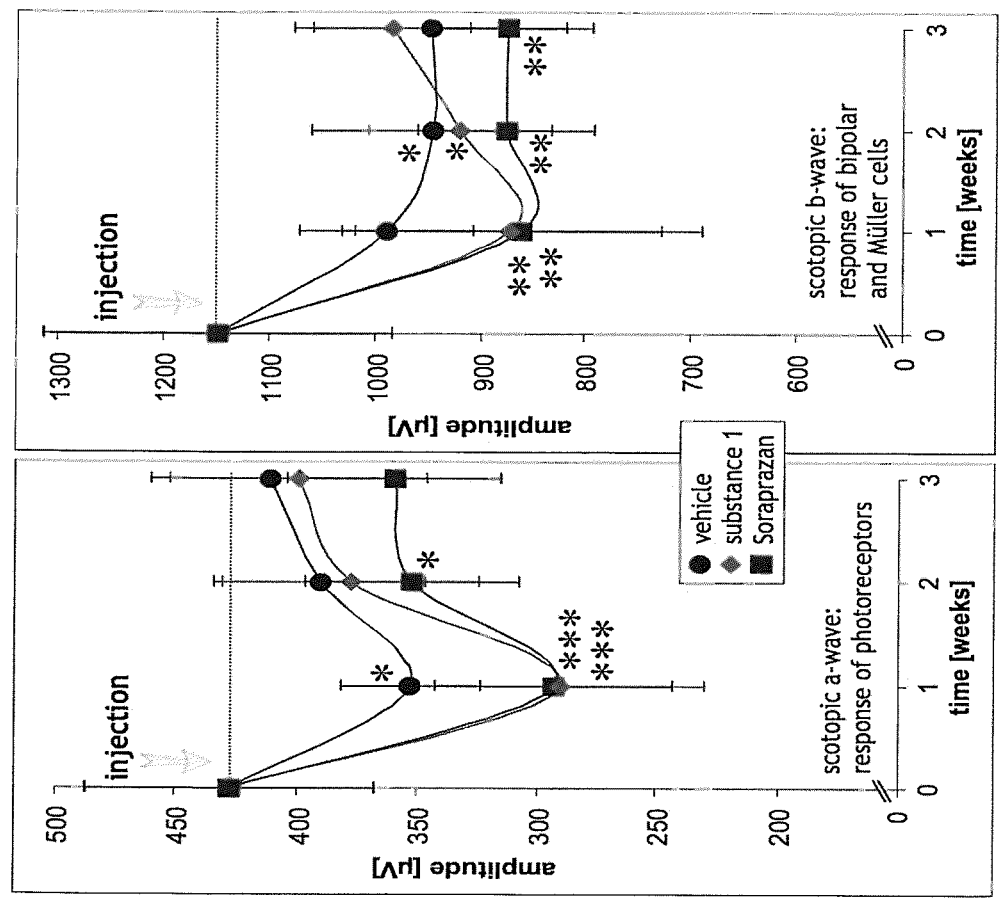
FIG. 20:
Soraprazan and substance 1 were injected into the vitreous of Wistar rats. The amplitudes of a-waves (photoreceptors) and b-waves (retinal neurons) are shown by electroretinography (ERG), recorded at the highest intensity of light stimulation. After an injection of vehicle solution (containing 20 vol % DMSO), a decrease of amplitudes is observed. If Soraprazan or substance 1 is injected, the decrease of the amplitudes is even more pronounced. During the following time, a certain recovery of the amplitudes can be observed. Amplitudes obtained in animals treated with vehicle or substance 1 solutions did recover almost completely three weeks after the injection, whereas the values obtained in Soraprazan-treated animals remained significantly lower than the base line.
Figure 21:
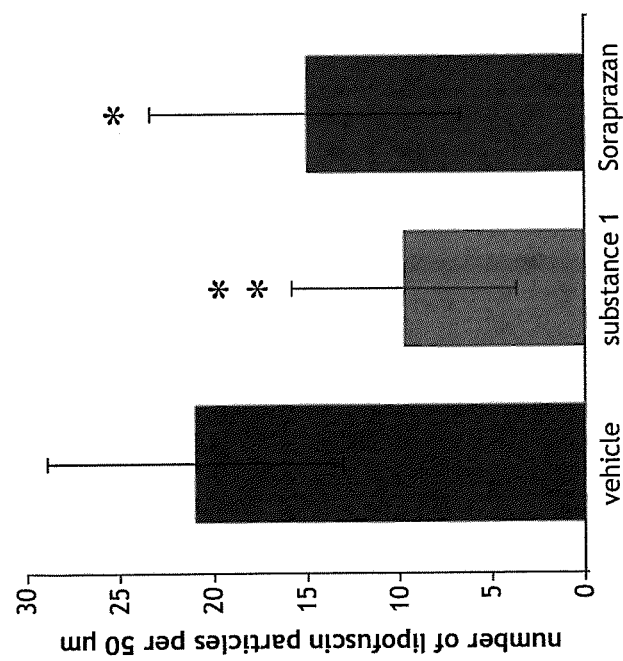
FIG. 21:
Soraprazan and substance 1 were injected into the vitreous of Wistar rats. The eyes were isolated after three weeks, fixed in formalin and embedded in paraffin. Paraffin sections were made, and digital fluorescence images were evaluated. The number of fluorescent lipofuscin particles per 50 μm RPE layer length was counted.
Figure 22:
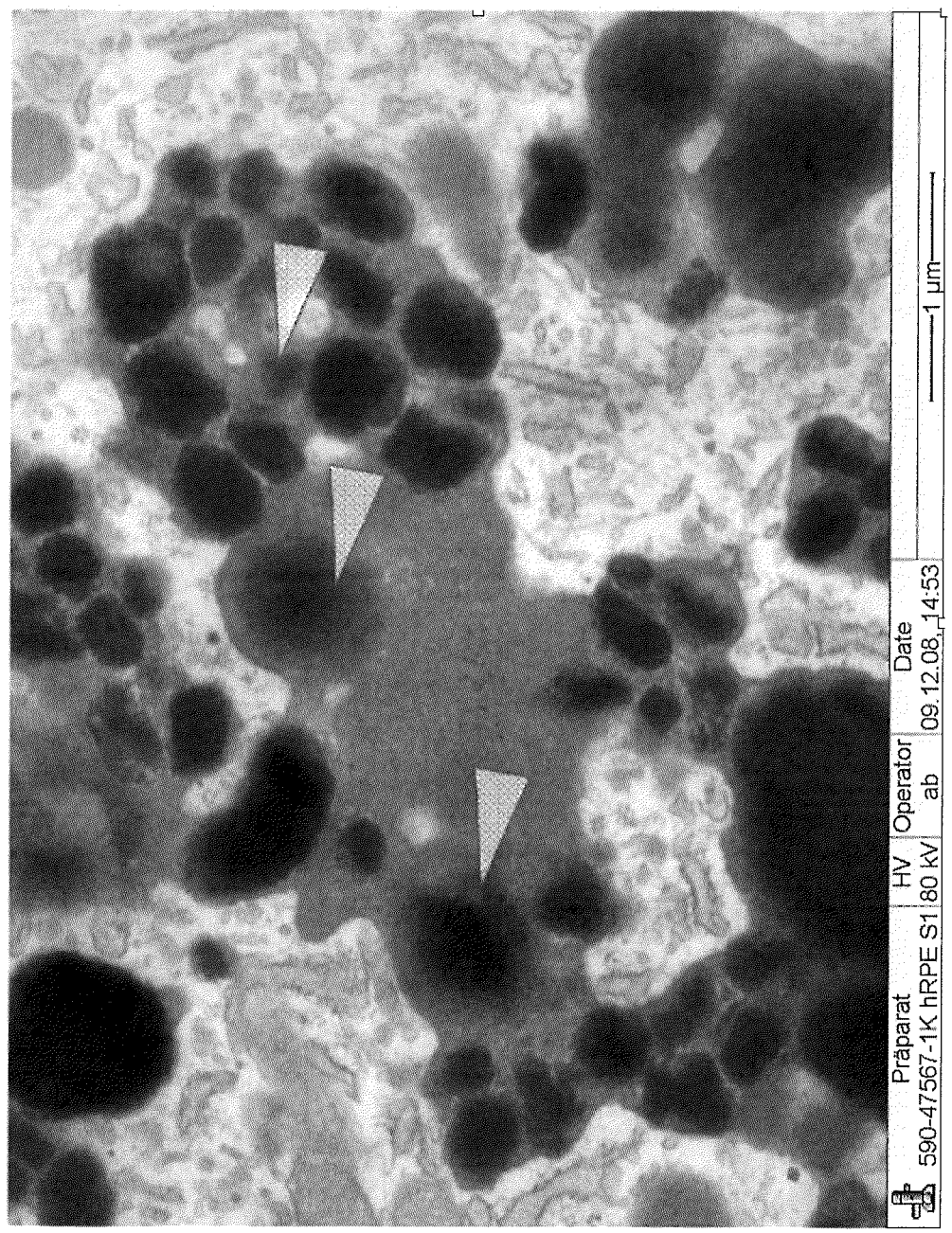
FIG. 22:
Human RPE cells treated with substance 1 contained clusters of pigment-like granules, covered by a limiting membrane as shown in an electron micrograph. These clusters contained unusual small melanin granules embedded into a lipofuscin-like electron opaque matrix indicating lipofuscin and melanin degradation. Some of these pigments don't have clear margins (arrowheads) which also indicates dissolution.

What is claimed is:

1. A method of treatment of dry AMD in a subject, comprising: administering to the subject in need of such treatment a medication comprising a compound according to the following formula I as active ingredient in suitable amount,

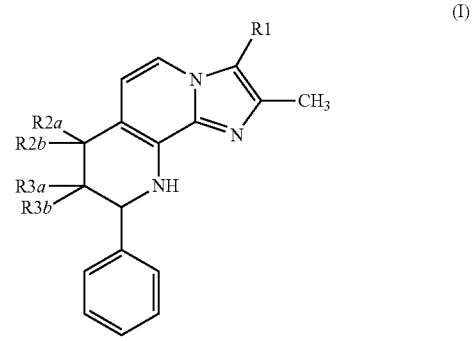

(I)

in which
R1 is methyl or hydroxymethyl, one of the substituents R2a and R2b is hydrogen and the other is hydroxy, methoxy, ethoxy, isopropoxy, methoxyethoxy or ethoxypropoxy, one of the substituents R3a and R3b is hydrogen and the other is hydroxy, methoxy, ethoxy, isopropoxy, methoxyethoxy or methoxypropoxy, where R2a or R2b on the one hand and R3a or R3b on the other hand are not simultaneously hydroxy, and its salts.

2. The method of claim 1, wherein R1 is methyl, one of the substituents R2a and R2b is hydrogen and the other is methoxy, ethoxy, isopropoxy, methoxyethoxy or methoxypropoxy, one of the substituents R3a and R3b is hydrogen and the other is hydroxy, and its salts.

3. The method according to claim 1, wherein R1 is methyl, one of the substituents R2a and R2b is hydrogen and the other is methoxy, ethoxy, isopropoxy, methoxyethoxy or methoxypropoxy, one of the substituents R3a and R3b is hydrogen and the other is methoxy, ethoxy, isopropoxy, methoxyethoxy or methoxypropoxy, and its salts.

4. The method according to claim 1, wherein R3b is hydrogen.

5. The method according to claim 1, wherein R2a and R3b are hydrogen.

6. The method according to claim 1, wherein R2a is hydrogen and R2b is methoxy, ethoxy, isopropoxy, methoxyethoxy or methoxypropoxy, and its salts.

7. A method of treatment of dry AMD in a subject, comprising: administering to the subject in need of such treatment a medication comprising a compound according to the following formula as active ingredient in a suitable amount,

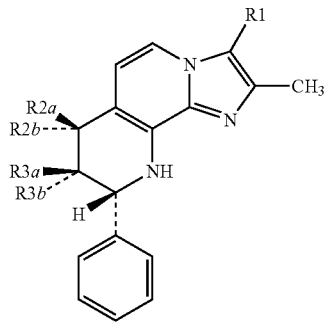 (I*)

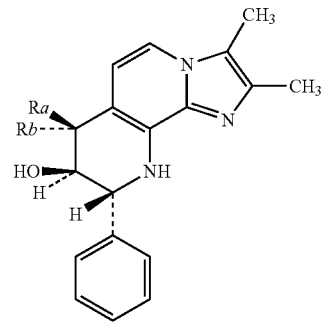 (I**)

in which R1 is methyl or hydroxymethyl, one of the substituents R2a and R2b is hydrogen and the other is hydroxy, methoxy, ethoxy, isopropoxy, methoxyethoxy or ethoxypropoxy, one of the substituents R3a and R3b is hydrogen and the other is hydroxy, methoxy, ethoxy, isopropoxy, methoxyethoxy or methoxypropoxy, where R2a or R2b on the one hand and R3a or R3b on the other hand are not simultaneously hydroxy, and its salts.

8. The method according to claim 7, wherein R1 is methyl, one of the substituents R2a and R2b is hydrogen and the other is methoxy, ethoxy, isopropoxy, methoxyethoxy or methoxypropoxy, one of the substituents R3a and R3b is hydrogen and the other is hydroxy, and its salts.

9. The method according to claim 7, wherein R1 is methyl, one of the substituents R2a and R2b is hydrogen and the other is methoxy, ethoxy, isopropoxy, methoxyethoxy or methoxypropoxy, one of the substituents R3a and R3b is hydrogen and the other is methoxy, ethoxy, isopropoxy, methoxyethoxy or methoxypropoxy, and its salts.

10. The method according to claim 7, wherein R3b is hydrogen.

11. The method according to claim 7, wherein R2a and R3b are hydrogen.

12. A method of treatment of dry AMD in a subject, comprising: administering to the subject in need of such treatment a medication comprising a compound according to the following formula I** as active ingredient in a suitable amount, wherein one of the substituents Ra and Rb is hydrogen and the other is methoxy, ethoxy, isopropoxy, methoxyethoxy or methoxypropoxy, and its salts.

13. The method according to claim 12, wherein Ra is hydrogen and Rb is methoxy, ethoxy, isopropoxy, methoxyethoxy or methoxypropoxy, and its salts.

14. The method according to claim 12, wherein the compounds according to formula I** is selected from (7R,8R,9R)-2,3-Dimethyl-8-hydroxy-7-(2-methoxyethoxy)-9-phenyl-7,8,9,10-tetrahydro-imidazo[1,2-h][1,7]naphthyridine and its salts or (7R,8R,9R)-2,3-Dimethyl-7-ethoxy-8-hydroxy-9-phenyl-7,8,9,10-tetrahydro-imidazo[1,2-h][1,7]naphthyridine and its pharmacologically acceptable salts.

15. The method of claim 1, wherein the medication is administered to the subject under treatment by way of administration selected from the group consisting of topical, intravitral, subretinal or periocular administration.

16. The method of claim 7, wherein the medication is administered to the subject under treatment by way of administration selected from the group consisting of topical, intravitral, subretinal or periocular administration.

17. The method of claim 12, wherein the medication is administered to the subject under treatment by way of administration selected from the group consisting of topical, intravitral, subretinal or periocular administration.

* * * * *